United States Patent
Gum

(10) Patent No.: US 10,051,427 B2
(45) Date of Patent: Aug. 14, 2018

(54) TECHNIQUES FOR PROVIDING LOCATION-BASED HEALTH ALERTS BASED ON BIOLOGICAL INDICATORS

(71) Applicant: QUALCOMM Incorporated, San Diego, CA (US)

(72) Inventor: Arnold Gum, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 15/243,322

(22) Filed: Aug. 22, 2016

(65) Prior Publication Data
US 2018/0054710 A1     Feb. 22, 2018

(51) Int. Cl.
| | | |
|---|---|---|
| H04W 4/02 | (2018.01) | |
| H04W 4/029 | (2018.01) | |
| A61B 5/00 | (2006.01) | |
| A61B 5/11 | (2006.01) | |
| G09B 19/00 | (2006.01) | |
| G09B 29/10 | (2006.01) | |
| H04W 4/04 | (2009.01) | |
| H04L 29/08 | (2006.01) | |

(52) U.S. Cl.
CPC .......... *H04W 4/029* (2018.02); *A61B 5/0022* (2013.01); *A61B 5/1123* (2013.01); *A61B 5/6898* (2013.01); *A61B 5/746* (2013.01); *G09B 19/0092* (2013.01); *G09B 29/102* (2013.01); *H04W 4/028* (2013.01); *A61B 2562/0219* (2013.01); *H04L 67/306* (2013.01); *H04W 4/04* (2013.01)

(58) Field of Classification Search
CPC ...... H04W 4/028; H04W 4/04; A61B 5/6898; A61B 5/746
USPC ......... 455/404.1, 404.2, 412.1, 456.1, 456.3, 455/41.1, 41.2, 521
See application file for complete search history.

(56) References Cited

U.S. PATENT DOCUMENTS

| | | |
|---|---|---|
| 2014/0012117 A1 | 1/2014 | Mensinger et al. |
| 2014/0247145 A1 | 9/2014 | Proud |
| 2014/0288436 A1 | 9/2014 | Venkatraman et al. |
| 2015/0039880 A1* | 2/2015 | Aminzade ........... H04L 41/0816 713/100 |
| 2015/0186636 A1* | 7/2015 | Tharappel ............... G06F 21/32 726/8 |
| 2015/0199493 A1 | 7/2015 | Glenn et al. |
| 2015/0223705 A1 | 8/2015 | Sadhu |

(Continued)

FOREIGN PATENT DOCUMENTS

WO    2016097376 A1    6/2016

OTHER PUBLICATIONS

International Search Report and Written Opinion—PCT/US2017/042780—ISA/EPO—dated Oct. 30, 2017.

*Primary Examiner* — Cong Tran
(74) *Attorney, Agent, or Firm* — Harrity & Harrity, LLP

(57) ABSTRACT

Certain aspects of the present disclosure generally relate to providing location-based health alerts based on biological indicators. In some aspects, a server may receive information that identifies a location associated with a mobile device. The server may determine a venue associated with the location. The server may identify health information associated with the venue. The health information may be based on data previously received in association with the venue. The server may provide a health alert based on the health information.

31 Claims, 13 Drawing Sheets

(56) References Cited

U.S. PATENT DOCUMENTS

| | | | | |
|---|---|---|---|---|
| 2015/0317855 | A1* | 11/2015 | Sezan | A61B 5/1171 340/5.52 |
| 2015/0382105 | A1* | 12/2015 | Thompson | A61B 5/1455 381/94.1 |
| 2016/0210434 | A1* | 7/2016 | Al-Sharif | G06F 19/3431 |
| 2016/0255944 | A1* | 9/2016 | Baranski | A44C 5/0069 |
| 2016/0317822 | A1* | 11/2016 | Rao | A61B 5/0031 |
| 2017/0124523 | A1* | 5/2017 | Yoon | G06Q 10/1095 |

\* cited by examiner

TECHNIQUES FOR PROVIDING LOCATION-BASED HEALTH ALERTS BASED ON BIOLOGICAL INDICATORS

FIELD OF THE DISCLOSURE

Aspects of the present disclosure generally relate to techniques for providing location-based health alerts, and more particularly to techniques for providing location-based health alerts based on biological indicators.

BACKGROUND

Certain activities, like eating particular foods or exercising, may cause a change in a biological indicator of a user, like blood pressure, glucose level, insulin level, heart rate, and/or the like. The user may not be aware of the impact that an activity has on the user's biological indicators prior to taking part in the activity (e.g., before eating a meal, before exercising, etc.). This can lead to a negative impact on the user's health.

SUMMARY

In some aspects, a server may include a memory and one or more processors coupled to the memory. The one or more processors may be configured to receive information that identifies a location associated with a mobile device. The one or more processors may be configured to determine a venue associated with the location, and to identify health information associated with the venue. The health information may be based on data previously received in association with the venue. The one or more processors may be configured to provide a health alert based on the health information.

In some aspects, a mobile device may include a memory and one or more processors coupled to the memory. The one or more processors may be configured to determine a location associated with the mobile device, and to access health information associated with the venue. The health information may be based on data previously received in association with the venue, and the venue may be associated with the location. The one or more processors may be configured to provide, based on the health information, a health alert.

In some aspects, a method may include determining, by a mobile device, a location associated with the mobile device. The method may include accessing, by the mobile device, health information associated with a venue. The health information may be based on data previously received in association with the venue, and the venue may be associated with the location. The method may include providing, by the mobile device and based on the health information, a health alert.

In some aspects, a method may include receiving, by a device, information that identifies a location associated with a mobile device. The method may include determining, by the device, a venue associated with the location. The method may include identifying, by the device, health information associated with the venue. The health information may be based on data previously received in association with the venue. The method may include providing, by the device and based on the health information, a health alert.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, both their organization and method of operation, together with associated advantages will be better understood from the following description when considered in connection with the accompanying figures. Each of the figures is provided for the purpose of illustration and description, and not as a definition of the limits of the claims.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects. The same reference numbers in different drawings may identify the same or similar elements.

DETAILED DESCRIPTION

The detailed description set forth below, in connection with the appended drawings, is intended as a description of various configurations and is not intended to represent the only configurations in which the concepts described herein may be practiced. The detailed description includes specific details for providing a thorough understanding of the various concepts. However, it will be apparent to those skilled in the art that these concepts may be practiced without these specific details.

Certain activities, like eating particular foods or exercising, may cause a change in a biological indicator of a user, like blood pressure, glucose level, insulin level, heart rate, and/or the like. The user may not be aware of the impact that an activity has on the user's biological indicators prior to taking part in the activity (e.g., before eating a meal, before exercising, etc.). This can lead to a negative impact on the user's health. Some activities may be associated with a venue at a particular geographic location. Aspects described herein use a geographic location associated with a user's mobile device to provide the user with predictive health alerts associated with the geographic location or a venue at the geographic location. Such health alerts may be determined or identified based on data previously received in association with the geographic location or venue, such as input provided by the user (e.g., via the mobile device), input provided by other users, measured biological indicators of the user or other users, and/or the like. In this way, a user may be alerted of activities that would have a negative impact on the user's health, and may avoid such activities.

Figure 1:
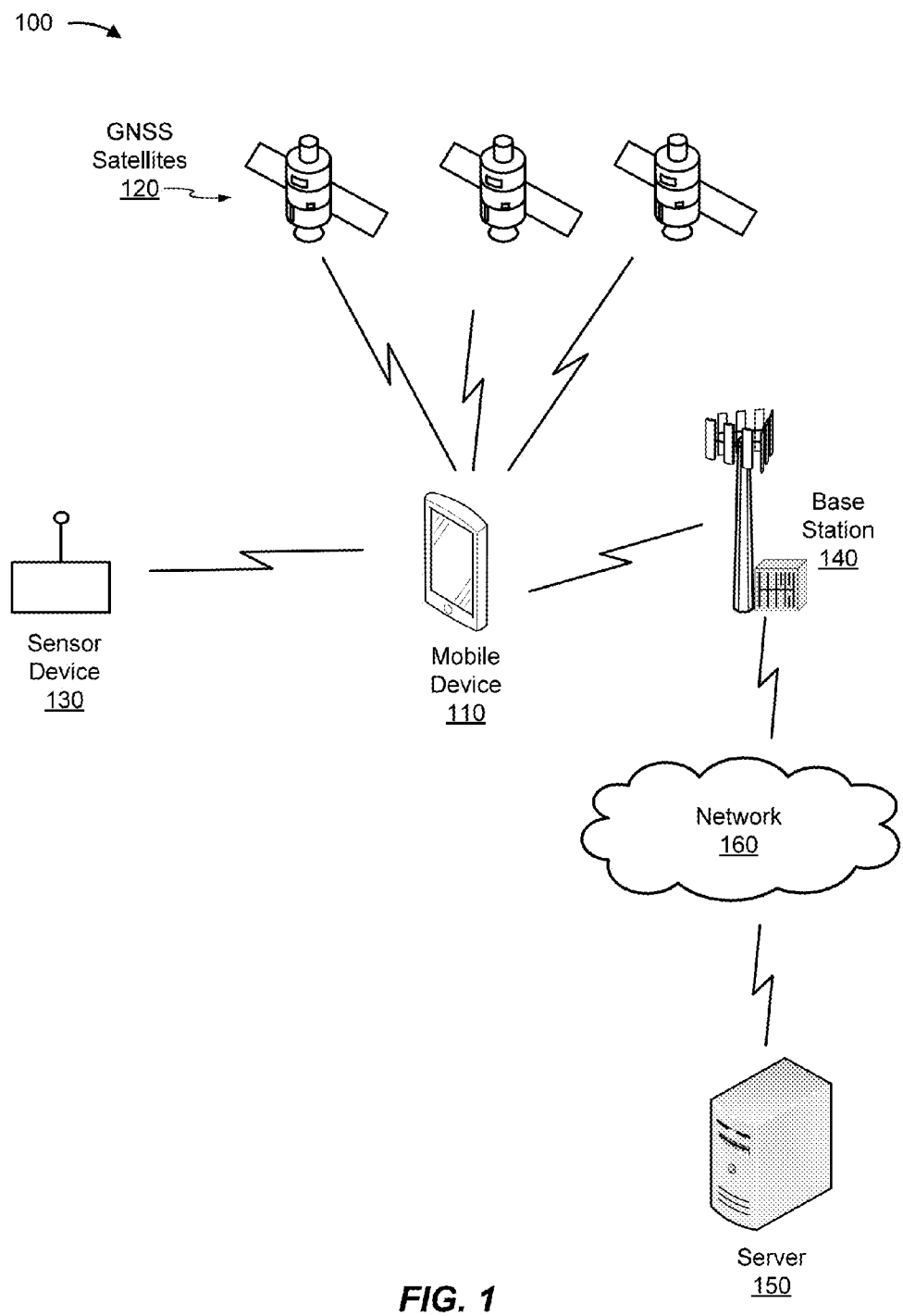
FIG. 1 is a diagram illustrating an example environment in which techniques described herein may be implemented, in accordance with various aspects of the present disclosure.

FIG. 1 is a diagram illustrating an example environment 100 in which techniques described herein may be implemented, in accordance with various aspects of the present disclosure. As shown in FIG. 1, environment 100 may include a mobile device 110, a set of Global Navigation Satellite System (GNSS) satellites 120, a sensor device 130, a base station 140, a server 150, and a network 160. Devices of environment 100 may interconnect via wired connections, wireless connections, or a combination of wired and wireless connections.

Mobile device 110 includes one or more devices capable of receiving, generating, storing, processing, and/or providing health information, health alerts, location information, or other types of information. For example, mobile device 110 may include a communication device (e.g., a wireless communication device), such as a mobile phone (e.g., a smart phone, a radiotelephone, etc.), a laptop computer, a tablet computer, a handheld computer, a gaming device, a wearable communication device (e.g., a smart wristwatch, a pair of smart eyeglasses, smart clothing, etc.), or a similar type of device. In some aspects, mobile device 110 may communicate with GNSS satellites 120 (e.g., to determine a location of mobile device 110), sensor device 130 (e.g., to receive sensor data associated with a biological indicator of a user), base station 140 (e.g., via an air interface), and/or server 150.

GNSS satellite 120 includes one or more satellites that form part of the GNSS. For example, GNSS satellite 120 may include a Global Positioning System (GPS) satellite, a Global Orbiting Navigation Satellite System (GLONASS) satellite, a Galileo satellite, and/or the like. GNSS satellites 120 may communicate with mobile device 110 to provide location information used to determine a geographic location of mobile device 110.

Sensor device 130 includes one or more devices used to sense or measure a biological indicator associated with a user. For example, sensor device 130 may include a heart rate monitor, a blood pressure sensor, a glucose monitor, a pulse monitor, an accelerometer, a pedometer, a gyroscope, a heat flux sensor, a skin conductivity sensor, a temperature sensor (e.g., a skin temperature sensor, an air temperature sensor, etc.), a calorie monitor, a sleep monitor, a motion sensor, a moisture sensor (e.g., a perspiration sensor), a chemical sensor or chemical compound sensor (e.g., to measure oxygen, carbon dioxide, lactate, testosterone, cortisol, glucose, glucagon, glycogen, insulin, starch, free fatty acid, triglycerides, monoglycerides, glycerol, pyruvate, lipids, other carbohydrates, ketone bodies, choline), a microphone (e.g., to detect noises from the stomach, a burp, passing gas, noises from a bathroom, etc.), and/or the like. In some aspects, sensor device 130 may measure or sense a parameter other than a biological indicator, such as an environmental parameter. In some aspects, sensor device 130 may be separate from mobile device 110, and may communicate with mobile device 110 (e.g., via a wired connection or a wireless connection). In some aspects, sensor device 130 may be integrated into mobile device 110.

Base station 140 includes one or more devices capable of transferring traffic, such as audio, video, text, and/or other traffic, destined for and/or received from mobile device 110. In some aspects, base station 140 may include an evolved Node B (eNB) associated with a long term evolution (LTE) network. In some aspects, base station 140 may be associated with a radio access technology (RAT) other than LTE. Base station 140 may send traffic to and/or receive traffic from mobile device 110 via an air interface (e.g., using radio waves), and may provide mobile device 110 with access to network 160. Base station 140 may transfer traffic between mobile device 110 and server 150 (e.g., via network 160). In some aspects, base station 140 may include a small cell base station, such as a base station of a microcell, a picocell, and/or a femtocell.

Server 150 includes one or more server devices capable of communicating with mobile device 110 (e.g., via base station 140 and network 160). For example, server 150 may include a host server, a web server, a server in a data center, a server in a cloud computing environment, and/or the like. In some aspects, server 150 may communicate with mobile device 110 to provide health alerts. Additionally, or alternatively, server 150 may host and/or access a data structure (e.g., a database) that stores health information, associated with multiple users and/or mobile device 110, to assist with providing health alerts. Additionally, or alternatively, server 150 may host and/or access a data structure that stores user profile information to assist with providing health alerts.

Network 160 includes one or more wired and/or wireless networks. For example, network 160 may include a cellular network (e.g., a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of environment 100 may perform one or more functions described as being performed by another set of devices of environment 100.

Figure 2:
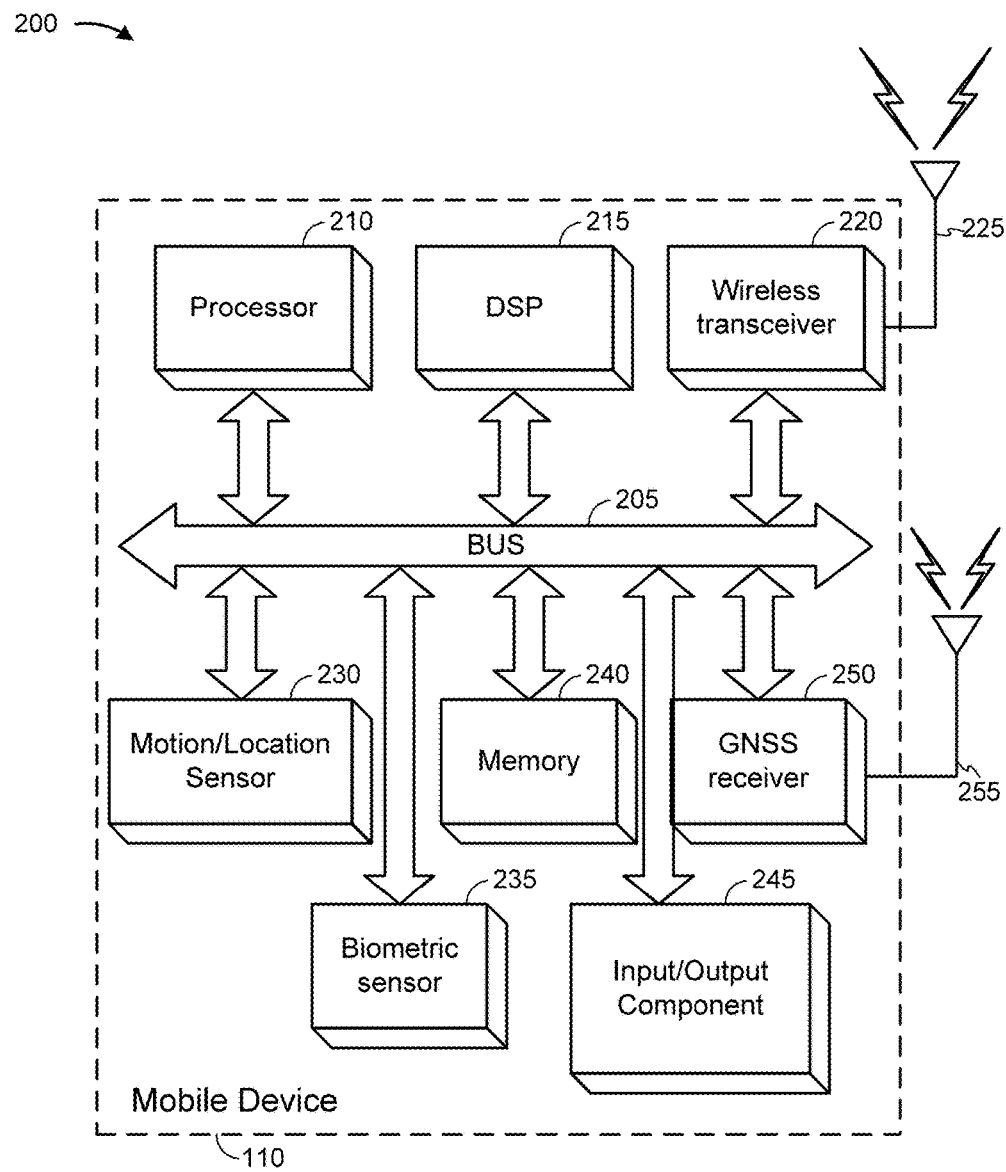
FIG. 2 is a diagram illustrating example components of a mobile device, in accordance with various aspects of the present disclosure.

FIG. 2 is a diagram illustrating example components of a device 200, in accordance with various aspects of the present disclosure. In some aspects, device 200 may correspond to mobile device 110. Additionally, or alternatively, device 200 may correspond to sensor device 130. As shown in FIG. 2, device 200 may include a bus 205, a processor 210, a digital signal processor (DSP) 215, a wireless transceiver 220, an antenna 225, a motion/location sensor 230, a biometric sensor 235, a memory 240, an input/output component 245, a GNSS receiver 250, a GNSS antenna 255, or any combination thereof.

Bus 205 includes one or more components that permit communication among the other components of device 200. For example, bus 205 may include an internal bus, an external bus, a parallel bus, a serial bus, a wire, an optical fiber, and/or the like.

Processor 210 includes one or more processors capable of interpreting and/or executing instructions, and/or capable of being programmed to perform one or more techniques described herein. For example, processor 210 may include a central processing unit (CPU), a graphics processing unit (GPU), an accelerated processing unit (APU), a microprocessor, a microcontroller, a field-programmable gate array (FPGA), an application-specific integrated circuit (ASIC), and/or the like. Processor 210 is implemented in hardware, firmware, or a combination of hardware and software. In some aspects, processor 210 may process location information (e.g., received from GNSS receiver 250) to determine a location associated with device 200. Processor 210 may use the location to determine a venue and/or to identify health information associated with the location or the venue, as described in more detail elsewhere herein.

DSP 215 includes one or more digital signal processors. For example, DSP 215 may include one or more processors 210 designed to perform digital signal processing. DSP 215 may measure, filter, and/or compress continuous real-world analog signals, such as signals received from one or more other components of device 200 (e.g., wireless transceiver 220, a motion/location sensor 230, biometric sensor 235, GNSS receiver 250, etc.).

Wireless transceiver 220 includes a transceiver and/or a separate receiver and transmitter that enables device 200 to communicate with other devices, such as via a wireless connection. Wireless transceiver 220 may permit device 200 to receive information from another device and/or provide information to another device. For example, wireless transceiver 220 may include a radio frequency (RF) communication component (e.g., a cellular modem), a Wi-Fi communication component, and/or the like.

Antenna 225 includes one or more antennas capable of transmitting or receiving information via an air interface (e.g., using radio waves). For example, device 200 (e.g., mobile device 110) may use antenna 225 to communicate with base station 140 to receive and/or provide information associated with health alerts. Additionally, or alternatively, device 200 (e.g., mobile device 110) may use antenna 225 to communicate with sensor device 130 to receive sensor data associated with one or more biological indicators of a user of device 200.

Motion/location sensor 230 includes one or more devices capable of measuring motion and/or location. For example, motion/location sensor 230 may include an accelerometer, a gyroscope, an altimeter, a motion sensor, a pedestrian dead reckoning (PDR) sensor, or the like. In some aspects, motion/location sensor 230 may be used to measure a movement of device 200. In this way, motion/location sensor 230 is capable of measuring movement of a user who is carrying device 200. In some aspects, motion/location sensor 230 may be used to determine whether device 200 is in motion or at rest. Additionally, or alternatively, motion/location sensor 230 may measure a speed or acceleration of the motion of device 200. This information may be used to determine an activity being performed by a user of device 200.

Biometric sensor 235 includes one or more biometric sensors capable of sensing or measuring a biological indicator associated with a user of device 200. For example, biometric sensor 235 may include a heart rate monitor, a blood pressure sensor, a glucose monitor, a pulse monitor, an accelerometer, a pedometer, a gyroscope, a heat flux sensor, a skin conductivity sensor, a temperature sensor, a calorie monitor, a sleep monitor, a motion sensor, a moisture sensor, a chemical sensor or chemical compound sensor, and/or the like, as described above in connection with sensor device 130.

Memory 240 includes a random access memory (RAM), a read only memory (ROM), and/or another type of dynamic or static storage device (e.g., a flash memory, a magnetic memory, and/or an optical memory). In some aspects, memory 240 may store information and/or instructions for use by processor 210. In some aspects, memory 240 includes a non-transitory computer-readable medium that stores instructions for execution by processor 210. When executed, the instructions may cause processor 210 to perform one or more operations described herein.

Input/output component 245 includes one or more input components and/or one or more output components. An input component includes a component that permits device 200 to receive information, such as via user input (e.g., a touch screen display, a keyboard, a keypad, a mouse, a button, a switch, and/or a microphone). An output component includes a component that provides output information from device 200 (e.g., a display, a speaker, and/or one or more light-emitting diodes (LEDs)). For example, input/output component 245 may be used to receive user input associated with health information and/or to output a health alert.

GNSS receiver 250 includes a receiver that enables device 200 to receive information from GNSS satellites 120. For example, GNSS receiver 250 may receive location information from a set of GNSS satellites 120, and may process the location information (e.g., using processor 210) to determine a geographic location of device 200. The geographic location may be used to determine a venue and/or health information associated with the location or the venue, as described in more detail elsewhere herein.

GNSS antenna 255 includes one or more antennas capable of receiving information, from GNSS satellites 120, via an air interface (e.g., using radio waves).

Figure 8:
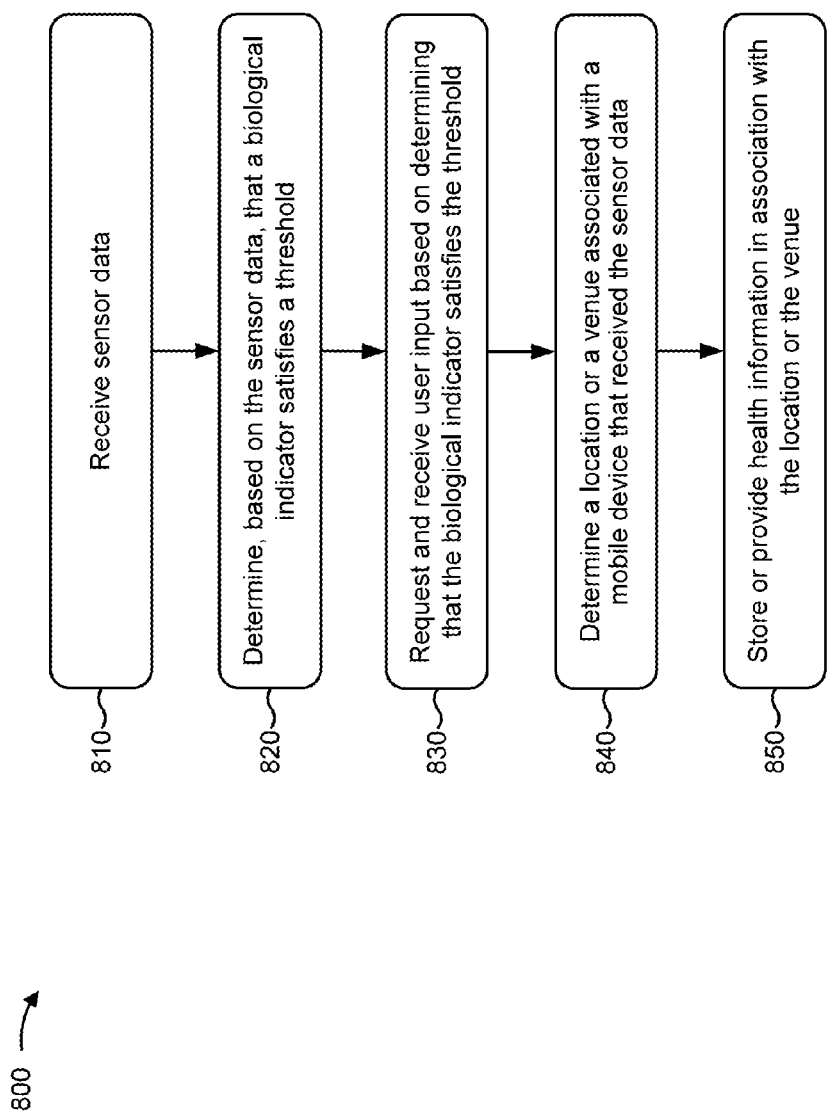
FIG. 8 is a diagram illustrating an example process for providing location-based health alerts, in accordance with various aspects of the present disclosure.
Figure 12:
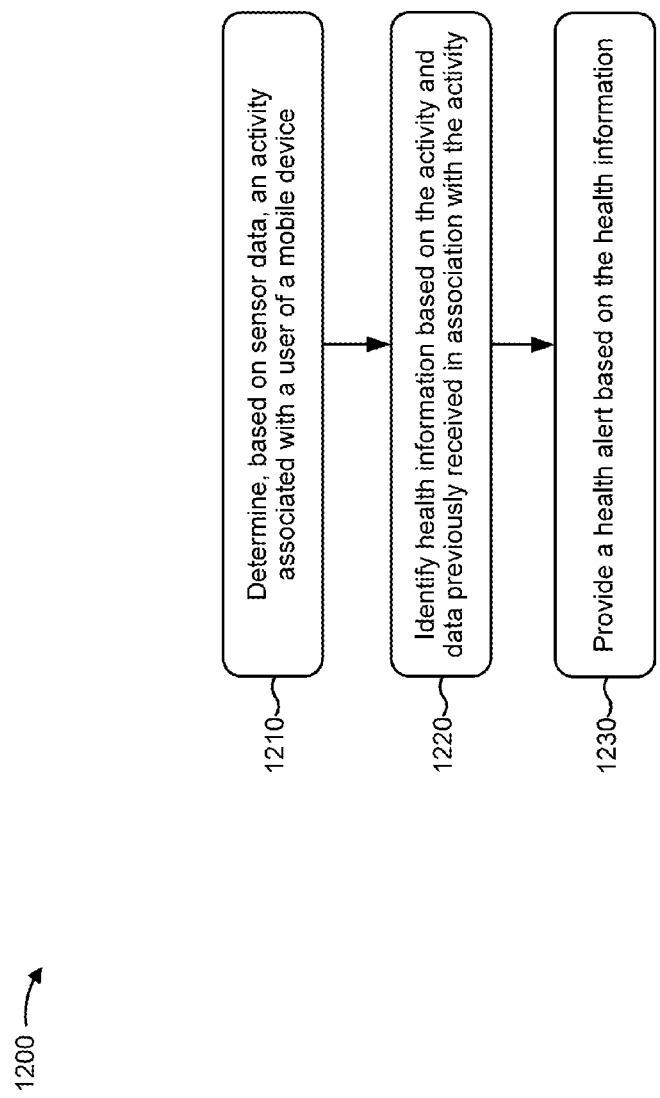
FIG. 12 is a diagram illustrating another example process for providing location-based health alerts, in accordance with various aspects of the present disclosure.

In some implementations, device 200 includes means for performing one or more processes described herein and/or means for performing one or more steps of the processes described herein, such as process 800 of FIG. 8, process 1200 of FIG. 12, and/or one or more other processes described herein. For example, the means for performing the processes and/or steps described herein may include bus 205, processor 210, DSP 215, wireless transceiver 220, antenna 225, motion/location sensor 230, biometric sensor 235, memory 240, input/output component 245, GNSS receiver 250, GNSS antenna 255, or any combination thereof.

The number and arrangement of components shown in FIG. 2 are provided as an example. In practice, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
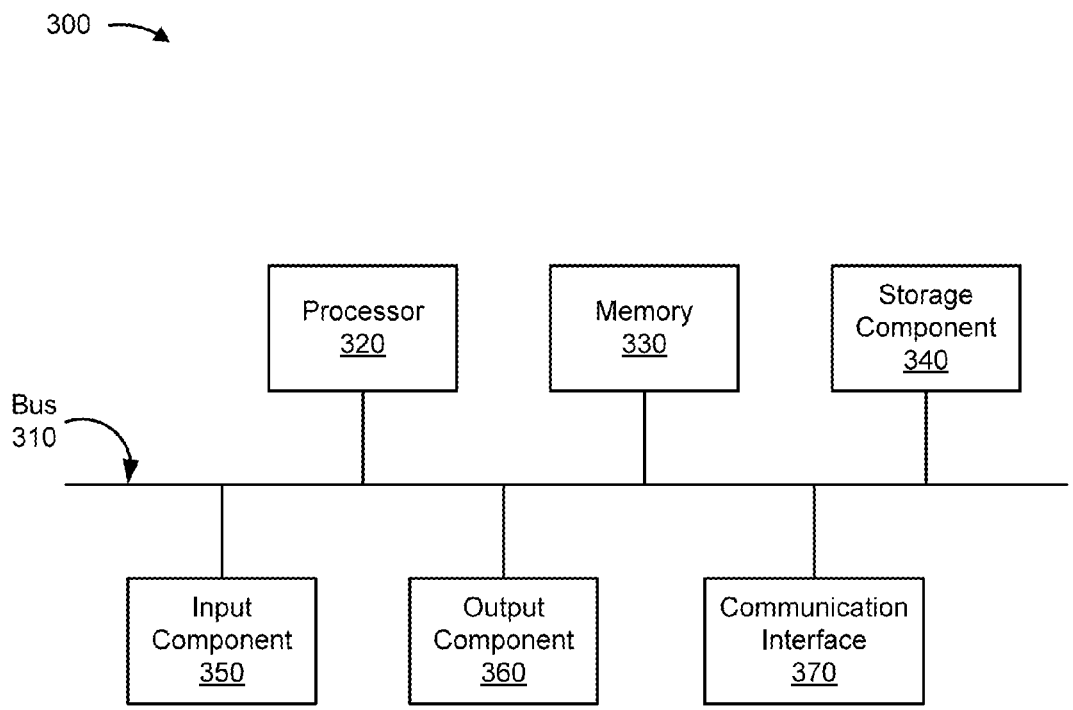
FIG. 3 is a diagram illustrating example components of one or more devices shown in FIG. 1, in accordance with various aspects of the present disclosure.

FIG. 3 is a diagram illustrating example components of a device 300, in accordance with various aspects of the present disclosure. Device 300 may correspond to mobile device 110, GNSS satellite 120, sensor device 130, base station 140, and/or server 150. In some implementations, mobile device 110, GNSS satellite 120, sensor device 130, base station 140, and/or server 150 may include one or more devices 300 and/or one or more components of device 300. As shown in FIG. 3, device 300 may include a bus 310, a processor 320, a memory 330, a storage component 340, an input component 350, an output component 360, a communication interface 370, or any combination thereof.

Bus 310 includes one or more components that permit communication among the other components of device 300.

Processor 320 includes one or more processors capable of interpreting and/or executing instructions, and/or capable of being programmed to perform one or more techniques described herein, such as a CPU, a GPU, an APU, a microprocessor, a microcontroller, an FPGA, an ASIC, and/or the like. Processor 320 is implemented in hardware, firmware, or a combination of hardware and software.

Memory 330 includes a RAM, a ROM, and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive. In some aspects, memory 330 and/or storage component 340 may store one or more data structures (e.g., databases) described herein, such as a data structure that stores health information, a data structure that stores user profile information, a data structure that stores venue and/or location information, or the like. In some aspects, these data structures may be stored in non-volatile memory (e.g., a hard drive, a flash drive, etc.).

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator).

Output component 360 includes a component that provides output information from device 300 (e.g., a display, a speaker, and/or one or more light-emitting diodes (LEDs)).

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

Figure 9:
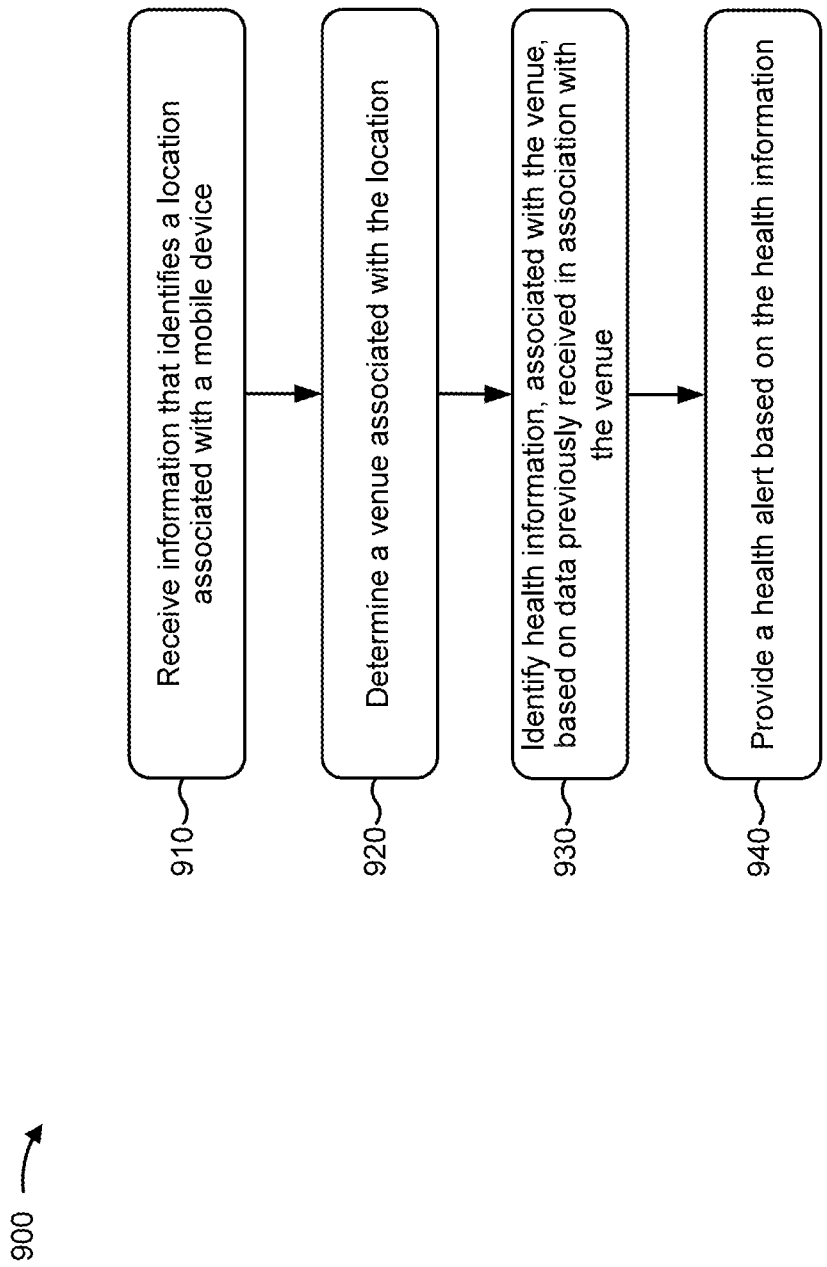
FIG. 9 is a diagram illustrating another example process for providing location-based health alerts, in accordance with various aspects of the present disclosure.
Figure 10:
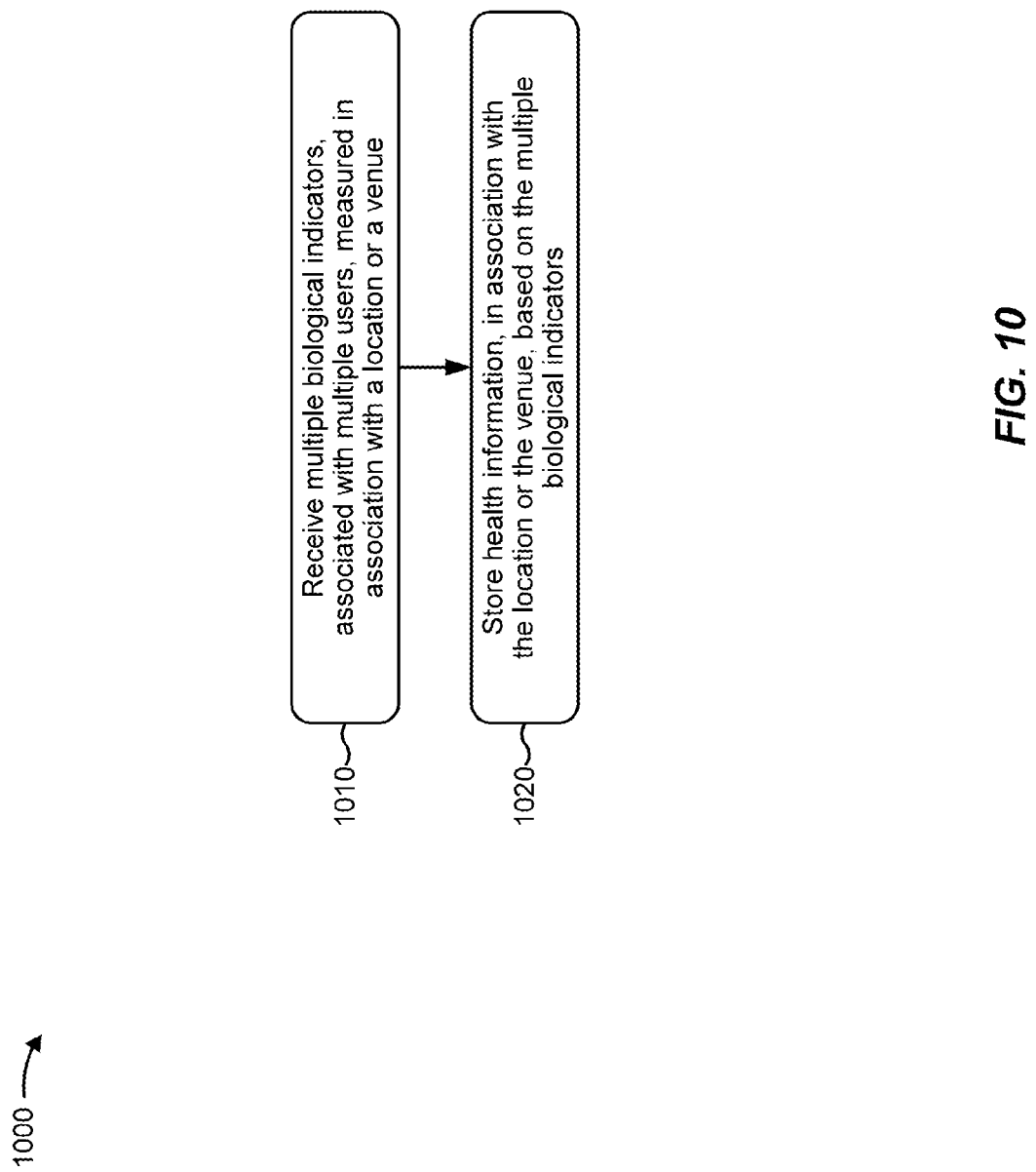
FIG. 10 is a diagram illustrating another example process for providing location-based health alerts, in accordance with various aspects of the present disclosure.
Figure 11:
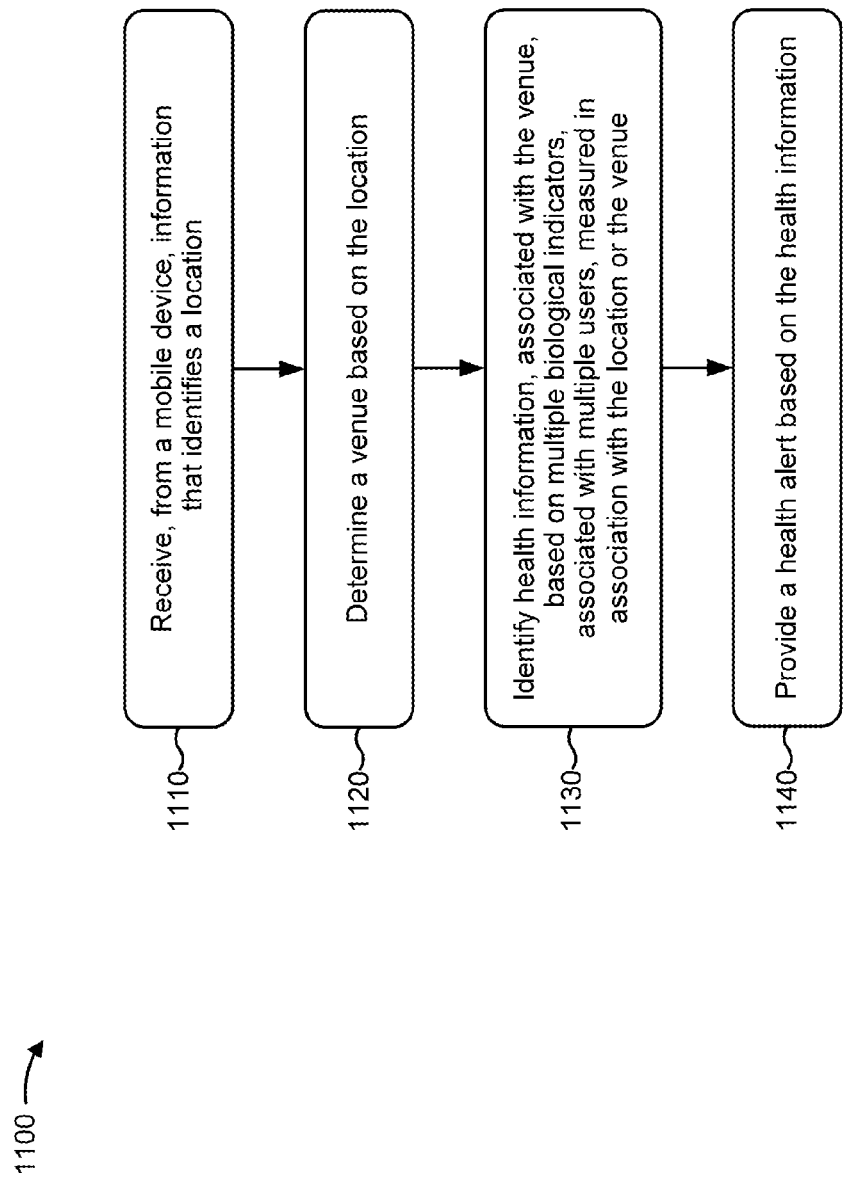
FIG. 11 is a diagram illustrating another example process for providing location-based health alerts, in accordance with various aspects of the present disclosure.
Figure 13:
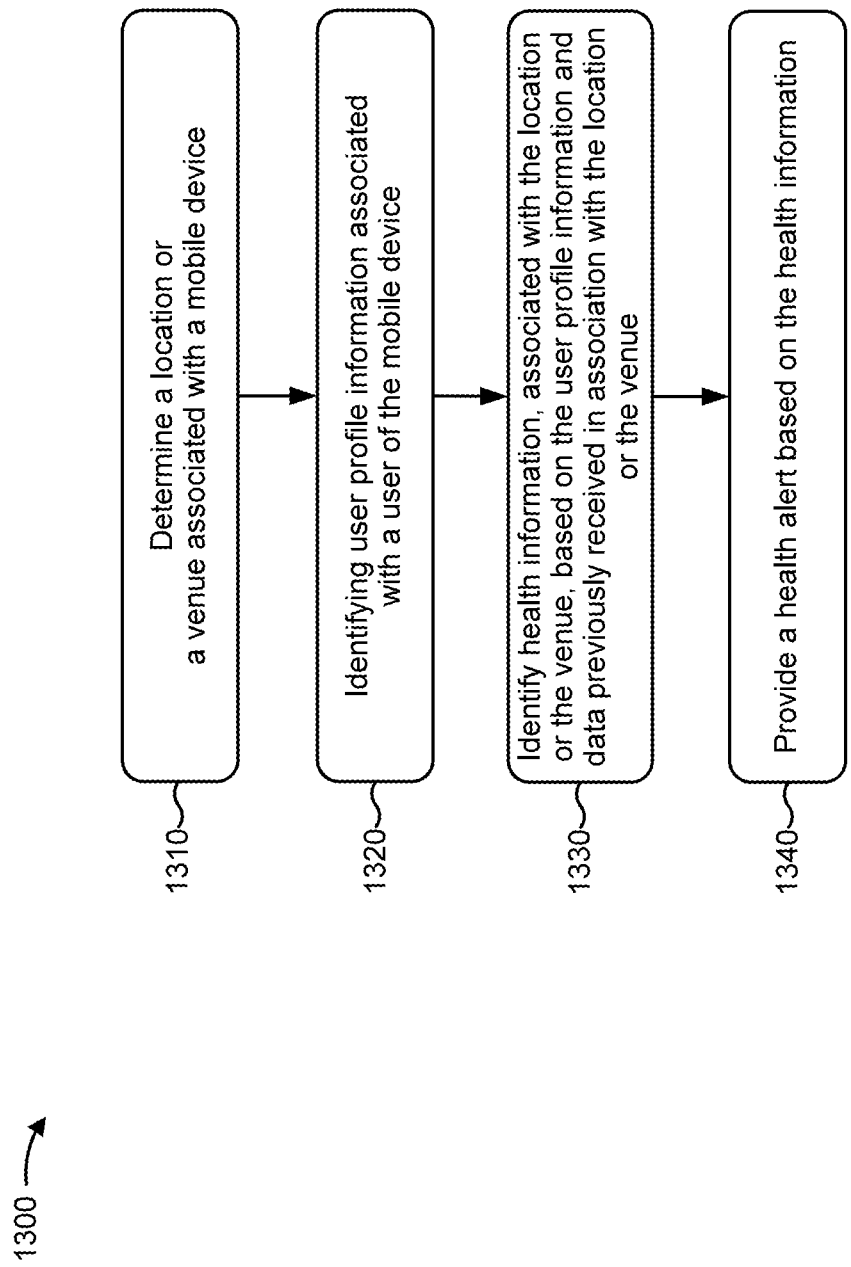
FIG. 13 is a diagram illustrating another example process for providing location-based health alerts, in accordance with various aspects of the present disclosure.

In some implementations, device 300 includes means for performing one or more processes described herein and/or means for performing one or more steps of the processes described herein, such as process 900 of FIG. 9, process 1000 of FIG. 10, process 1100 of FIG. 11, process 1300 of FIG. 13, and/or one or more other processes described herein. For example, the means for performing the processes and/or steps described herein may include bus 310, processor 320, memory 330, storage component 340, input component 350, output component 360, communication interface 370, or any combination thereof.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
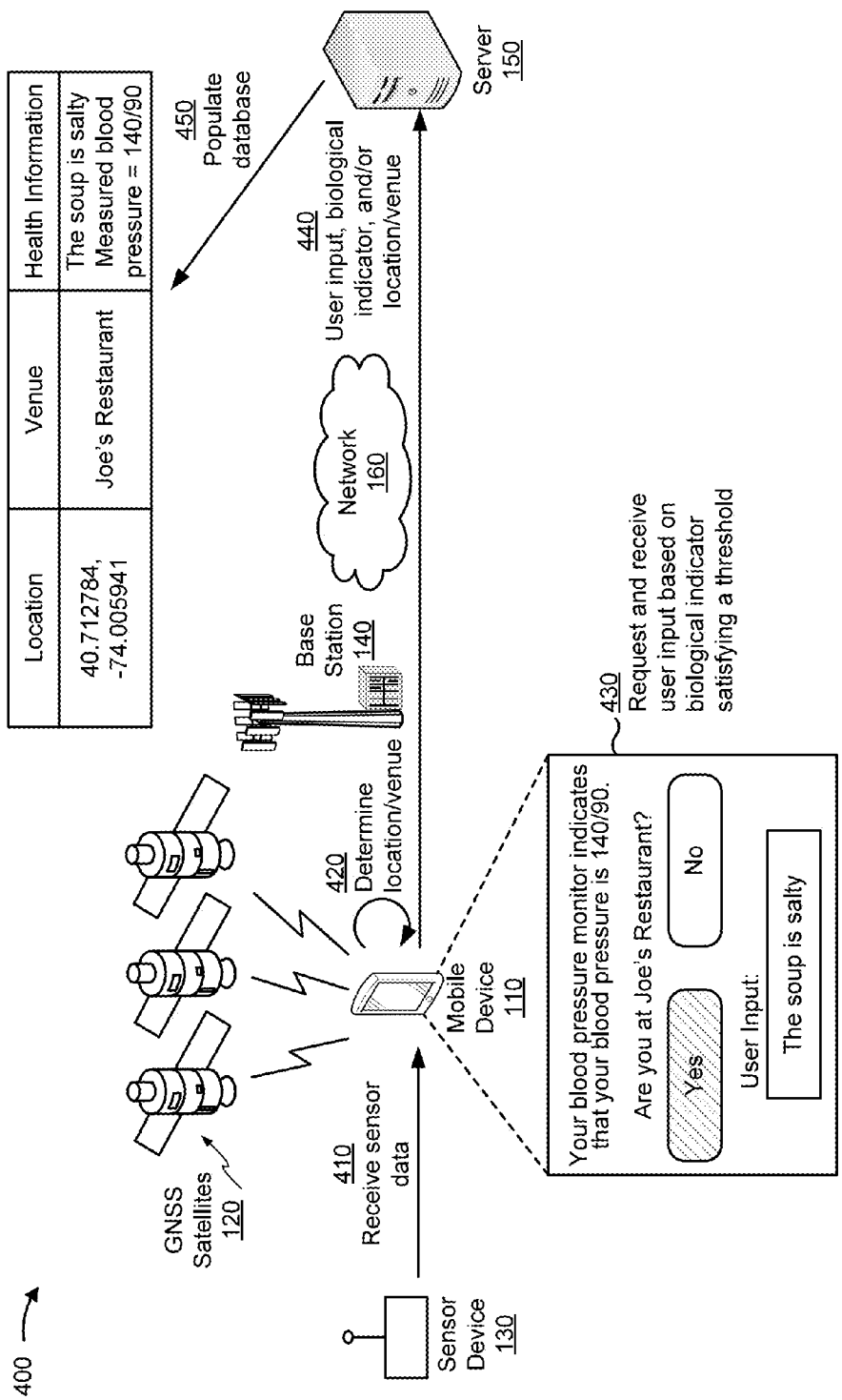
FIG. 4 is a diagram illustrating an example of providing location-based health alerts, in accordance with various aspects of the present disclosure.

FIG. 4 is a diagram illustrating an example 400 of providing location-based health alerts, in accordance with various aspects of the present disclosure. FIG. 4 shows an example of populating a database with health information and associating the health information with a location and/or a venue. In this way, health alerts can be provided in association with the location and/or the venue (e.g., when mobile device 110 is located at the location and/or venue).

As shown in FIG. 4, and by reference number 410, mobile device 110 may receive sensor data from sensor device 130. The sensor data may include data measured or sensed by sensor device 130, such as a biological indicator associated with a user. The biological indicator may relate to the user's health. For example, the biological indicator may indicate a heart rate of the user, a blood pressure of the user, a glucose level of the user (e.g., a blood glucose level), a pulse of the user, movement of the user (e.g., a speed of movement, a direction of movement, etc.), a quantity of steps taken by the user, a heat flux measurement associated with the user, a skin conductivity measurement associated with the user, a temperature associated with the user (e.g., a body temperature, a skin temperature, an environmental temperature, etc.), a calorie measurement associated with the user (e.g., a quantity of calories burned), a sleep measurement associated with the user (e.g., a quantity of hours slept, a sleep quality measurement based on movement of the user, etc.), a moisture measurement associated with the user (e.g., a measurement of skin perspiration, a humidity measurement, etc.), a measurement of a chemical level associated with the user, and/or the like.

For the purpose of FIG. 4, assume that sensor device 130 includes a blood pressure monitor that measures the user's blood pressure. Mobile device 110 may receive one or more blood pressure measurements from sensor device 130 (e.g., periodically). Mobile device 110 may determine that the sensor data (e.g., the blood pressure measurement) satisfies a threshold (e.g., that the user's blood pressure measurement satisfies a threshold, that the user's blood pressure increased or decreased by an amount that satisfies a threshold, that a set of the user's blood pressure measurements satisfies a threshold for a particular amount of time or for a particular number of blood pressure measurements, that a user's blood pressure has changed by a threshold amount relative to a baseline, such as a baseline measured over a period of time, etc.), and may determine a location or a venue associated with mobile device 110 based on the determination, as shown by reference number 420. For example, mobile device 110 may communicate with multiple GNSS satellites 120 to determine a location of mobile device 110. Additionally, or alternatively, mobile device 110 may use the location to identify a venue associated with the location (e.g., based on information stored in a data structure). In some aspects, mobile device 110 may identify a venue based on detecting an access point (e.g., a Wi-Fi access point) associated with the venue.

As shown by reference number 430, mobile device 110 may request and receive user input based on determining that the measured biological indicator satisfies a threshold. For example, mobile device 110 may request the user input based on determining that the user's blood pressure is greater than or equal to 140 over 90 millimeters of mercury (mmHg). In some aspects, the threshold may be an absolute threshold (e.g., 140, 90, etc.). In some aspects, the threshold may be a relative threshold as compared to a baseline for the user. For example, the user may have a baseline blood pressure of 110 over 60, which may be determined based on user input, based on measuring the user's blood pressure over a period of time, or the like. In this case, the threshold may be based on a rise of blood pressure of, for example, 20 points, or 130 over 80. As shown, mobile device 110 may alert the user regarding the measured biological indicator by providing an indication of the measured biological indicator for display. Additionally, or alternatively, mobile device 110 may provide a user interface to obtain user input, such as a confirmation of the user's location or a venue where the user is located (e.g., shown as "Joe's Restaurant") and/or freeform input (e.g., text input), shown as "The soup is salty." In some aspects, the user may interact with mobile device 110 to provide the user input without mobile device 110 first detecting that a biological indicator satisfies a threshold.

As shown by reference number 440, mobile device 110 may provide, to server device 150 and via base station 140 and network 160, the user input, information that identifies the measured biological indicator, information that identifies the location of mobile device 110, and/or information that identifies a determined venue associated with the location. In some aspects, mobile device 110 may provide information that identifies the location, and server 150 may identify a venue associated with the location (e.g., based on information stored in a data structure).

As shown by reference number 450, server 150 may populate one or more databases or other data structures with location information (e.g., information that identifies a location of mobile device 110, such as by using GPS coordinates, a set of map tiles, a geofence, and/or the like), venue information (e.g., information that identifies a venue associated with the location), and health information. The health information may include the measured biological indicator (e.g., the measured blood pressure, as shown) and/or the user input (e.g., "The soup is salty"). Server 150 may associate the location, the venue, and/or the health information in the database.

In this way, server 150 may populate a database that stores health information associated with a location and/or a venue. Server 150 may populate the database with health information, which may be used to provide health alerts to mobile devices 110 (e.g., the illustrated mobile device 110 or other mobile devices 110) when those mobile devices 110 are located at the location and/or the venue. In this way, a user of mobile device 110 can receive predictive health alerts associated with locations or venues, so that the user can make intelligent health-related decisions at those locations or venues. Furthermore, computing resources may be saved by proactively providing health alerts rather than consuming computing resources based on a user search for information.

As indicated above, FIG. 4 is provided as an example. Other examples are possible and may differ from what was described in connection with FIG. 4.

Figure 5:
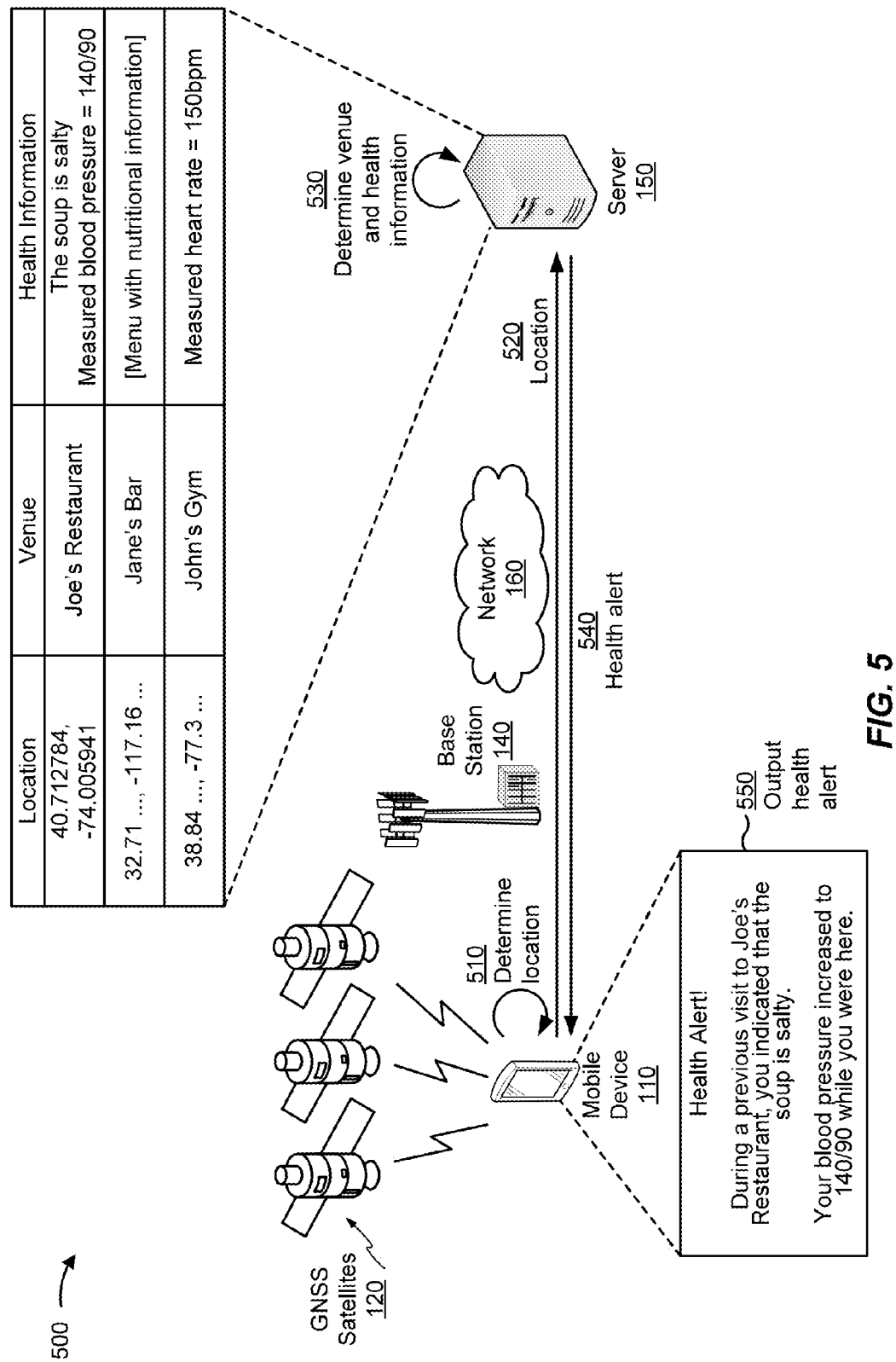
FIG. 5 is a diagram illustrating another example of providing location-based health alerts, in accordance with various aspects of the present disclosure.

FIG. 5 is a diagram illustrating another example 500 of providing location-based health alerts, in accordance with various aspects of the present disclosure. FIG. 5 shows an example of identifying health information, associated with a location and/or a venue, based on data previously received in association with the location or the venue. FIG. 5 further shows providing a health alert based on the health information.

As shown in FIG. 5, and by reference number 510, assume that mobile device 110 determines a location of mobile device 110. For example, mobile device 110 may communicate with multiple GNSS satellites 120 to determine a location of mobile device 110. In some aspects, mobile device 110 may use the location to identify a venue associated with the location (e.g., based on information stored in a data structure).

As shown by reference number 520, mobile device 110 may provide, to server 150 (e.g., via base station 140 and network 160), information that identifies the location. In some aspects, such as when mobile device 110 determines a venue associated with the location, mobile device 110 may provide, to server 150 (e.g., via base station 140 and network 160), information that identifies the venue. In some aspects, server 150 may determine the venue based on the location.

As shown by reference number 530, server 150 may determine the venue, based on the location, and may identify health information based on the location and/or the venue. For example, server 150 may identify the health information by performing a lookup in a database that stores the health information in association with the location and/or the venue.

For the purpose of FIG. 5, assume that mobile device 110 is located in a location identified by the GPS coordinates 40.712784 latitude and −77.005941 longitude, which corresponds to a venue of "Joe's Restaurant." Using this location and/or venue, server 150 identifies data previously received in association with the location and/or venue. For example, server 150 may identify health information based on previously received user input indicating that "The soup is salty," and further based on a previously measured biological indicator received in association with the venue, such as a measured blood pressure of 140 over 90 mmHg while mobile device 110 was located in the location and/or venue, a measured increase of the user's blood pressure (e.g., from 120 over 70 to 40 over 90 mmHg), a percentage increase of the user's blood pressure, and/or the like.

As shown by reference number 540, server 150 may provide, to mobile device 110, a health alert. The health alert may be based on the health information. For example, the health alert may include at least a portion of the user input, may include the measured biological indicator, or may include the health information.

As shown by reference number 550, mobile device 110 may output the health alert (e.g., on a display of mobile device 110). For example, the health alert displayed by mobile device 110 indicates that during a previous visit to Joe's Restaurant, the user indicated that the soup is salty, and that sensor device 130 measured a blood pressure of 140 over 90 mmHg for the user. As another example, the health alert may indicate a measured increase of the user's blood pressure (e.g., from 120 over 70 to 40 over 90 mmHg), a percentage increase of the user's blood pressure, and/or the like.

In this way, a user of mobile device 110 may be provided with predictive health alerts so that the user can make healthy decisions. For example, the user may avoid eating an unhealthy food (e.g., the salty soup), may avoid a particular venue (e.g., Joe's Restaurant) for health reasons, may take medication (e.g., blood pressure medication) prior to visiting a venue or participating in an activity at the venue (e.g., eating, drinking, exercising, etc.), and/or the like.

As indicated above, FIG. 5 is provided as an example. Other examples are possible and may differ from what was described in connection with FIG. 5.

Figure 6:
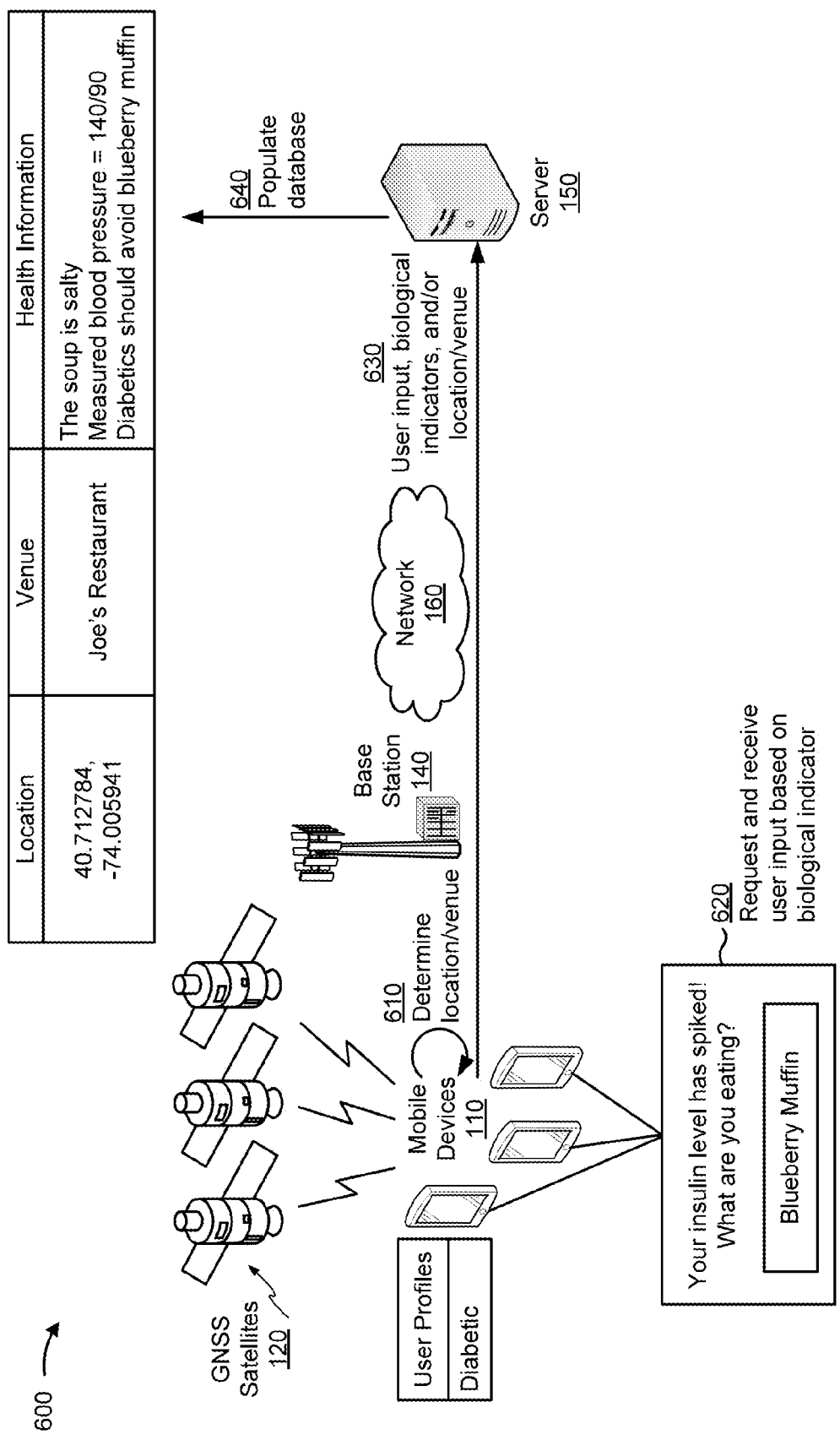
FIG. 6 is a diagram illustrating another example of providing location-based health alerts, in accordance with various aspects of the present disclosure.

FIG. 6 is a diagram illustrating another example 600 of providing location-based health alerts, in accordance with various aspects of the present disclosure. FIG. 6 shows an example of populating a database with health information based on user input (e.g., text input, measured biological indicators, etc.) received from multiple mobile devices 110, and associating the health information with a location and/or a venue. In this way, crowd-sourced health alerts can be provided in association with the location and/or the venue (e.g., when mobile device 110 is located at the location and/or venue).

As shown in FIG. 6, and by reference number 610, mobile device 110 may determine a location and/or a venue of mobile device 110. For example, mobile device 110 may communicate with multiple GNSS satellites 120 to determine a location of mobile device 110. In some aspects, mobile device 110 may use the location to identify a venue associated with the location (e.g., based on information stored in a data structure).

As shown by reference number 620, mobile device 110 may request and receive user input associated with the location (e.g., based on a biological indicator satisfying a threshold, such as an absolute threshold or a relative threshold). For example, mobile device 110 may request the user input based on determining that a user's insulin level has spiked (e.g., has increased by a threshold amount, has increased to a level that satisfies a threshold, etc.). As shown, mobile device 110 may alert the user regarding the measured biological indicator by providing an indication of the measured biological indicator for display. Additionally, or alternatively, mobile device 110 may provide a user interface to obtain user input, such as information that identifies an activity that the user is performing (e.g., shown as eating a blueberry muffin).

As shown by reference number 630, mobile device 110 may provide, to server device 150 and via base station 140 and network 160, the user input, information that identifies the measured biological indicator, information that identifies the location of mobile device 110, and/or information that identifies a determined venue associated with the location. In some aspects, mobile device 110 may provide information that identifies the location, and server 150 may identify a venue associated with the location (e.g., based on information stored in a data structure).

As shown, server 150 may receive this information from multiple mobile devices 110 associated with multiple users. For example, server 150 may receive the information over a period of time. In some aspects, server 150 may determine user profile information associated with mobile device 110. The user profile information may indicate a health condition of a user of mobile device 110 (e.g., diabetic, allergies, high blood pressure, one or more medications being taken by the user, etc.), health preferences and/or activity preferences associated with the user (e.g., a type of food or drinks that the user enjoys, a manner in which the user likes his or her meals prepared, a type of exercise that the user enjoys, etc.), and/or the like.

As shown by reference number 640, server 150 may populate one or more databases or other data structures with location information (e.g., information that identifies a location of mobile device 110, such as by using GPS coordinates or other coordinates), venue information (e.g., information that identifies a venue associated with the location), and health information. The health information may include the measured biological indicator (e.g., a measured insulin level) and/or the user input (e.g., "blueberry muffin"). Server 150 may associate the location, the venue, and/or the health information in the database.

In some aspects, server 150 may associate the health information with user profile information. For example, some health information may only apply to users with a particular health condition. In this case, server 150 may store information that identifies the health condition or other user profile information in association with the health information. For example, server 150 may store an indication that users who are diabetic should avoid the blueberry muffin at Joe's Restaurant, as shown. This may conserve memory resources by only storing the health information in association with users with particular user profile information, rather than across all users.

In this way, server 150 may populate a database that stores health information associated with a location and/or a venue. Server 150 may populate the database with health information received from multiple mobile devices 110 associated with multiple users. This health information may be used to provide health alerts to mobile devices 110 (e.g., the illustrated mobile devices 110 or other mobile devices 110) when those mobile devices 110 are located at the location and/or the venue. In this way, a user of mobile device 110 can receive predictive health alerts associated with locations or venues even if the user has not previously visited the location or venue (e.g., based on health information associated with other users, such as other users who have user profile information in common with the user). In some aspects, server 150 may selectively provide the health alert, such as when the health alert is applicable to the user, thereby conserving computing resources and network resources by preventing transmission of health alerts that are not applicable to a user.

As indicated above, FIG. 6 is provided as an example. Other examples are possible and may differ from what was described in connection with FIG. 6.

Figure 7:
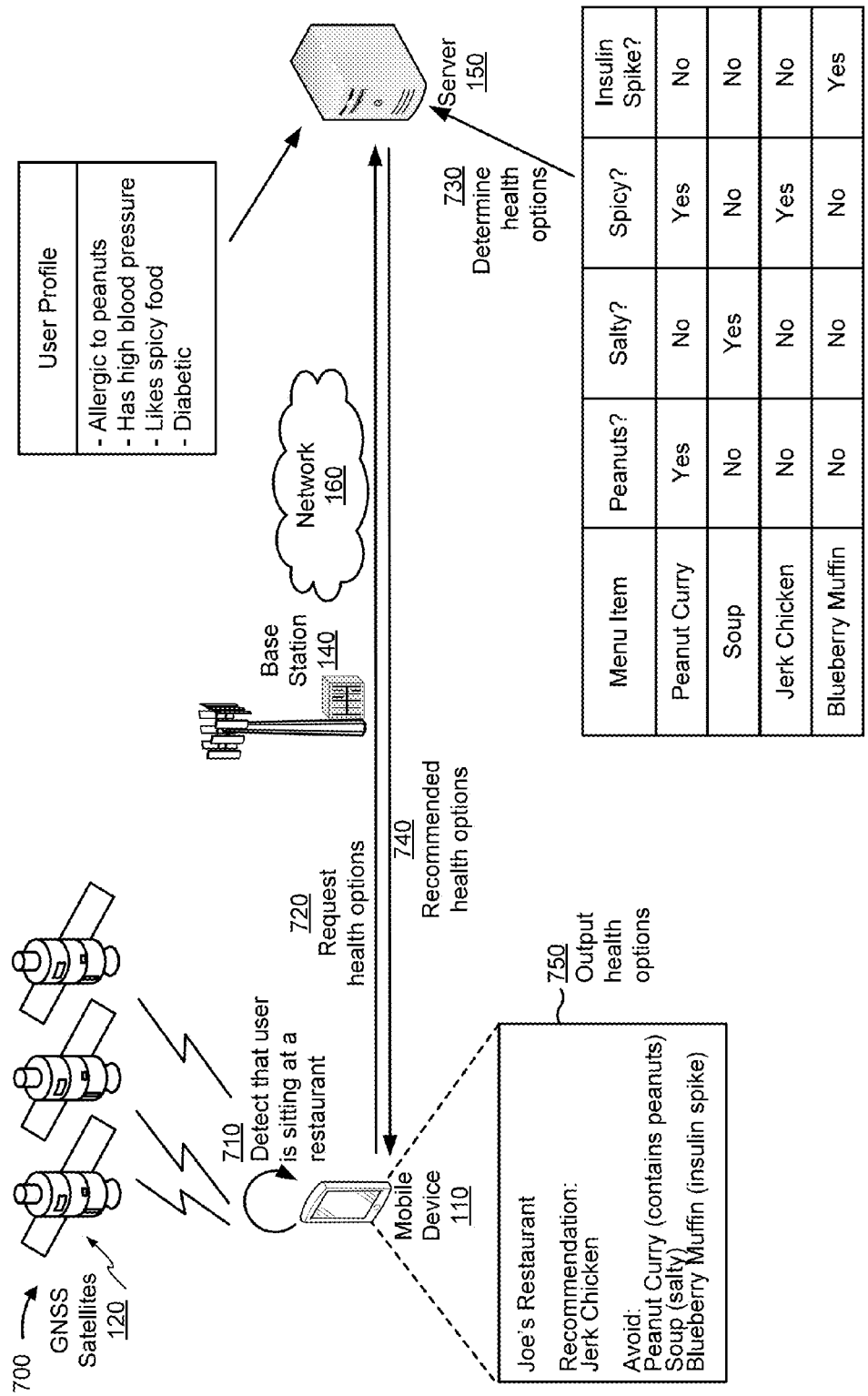
FIG. 7 is a diagram illustrating another example of providing location-based health alerts, in accordance with various aspects of the present disclosure.

FIG. 7 is a diagram illustrating another example 700 of providing location-based health alerts, in accordance with various aspects of the present disclosure. FIG. 7 shows an example of determining recommended health options associated with a location and/or venue, and providing the recommended health options to mobile device 110 as a health alert. In some aspects, the recommended health options may be determined based on user profile information.

As shown in FIG. 7, mobile device 110 may determine that a user is sitting at a restaurant. In some aspects, mobile device 110 may use location information (e.g., received from GNSS satellites 120) to determine that mobile device 110 is located in a restaurant. Additionally, or alternatively, mobile device 110 may use one or more sensors to determine that the user is sitting, such as motion/location sensor 230 that indicates that the user is not in motion.

As shown by reference number 720, mobile device 110 may request, from server 150, health options associated with the restaurant. For example, mobile device 110 may request the health options based on determining that the user is sitting in the restaurant. Additionally, or alternatively, mobile device 110 may request the health options based on input received from the user (e.g., via a user interface).

As shown by reference number 730, server 150 may determine one or more health options based on the request. For example, the health options may indicate a type of food (or drink) to eat, a type of food (or drink) to avoid, a particular menu item to eat or avoid (e.g., based on menu information determined based on a location or venue of mobile device 110), a type of exercise to perform, a type of exercise to avoid, a type of activity to perform, a type of activity to avoid, and/or the like.

In some aspects, server 150 may determine the health options based on data previously received in associated with the venue. For example, a user may indicate a food that the user liked or did not like, and server 150 may recommend that food or a similar food (e.g., based on characteristics of the food). Additionally, or alternatively, server 150 may determine the health options based on user profile information associated with a user of mobile device 110.

As an example, and as shown, assume that user profile information indicates that the user is allergic to peanuts, has high blood pressure, likes spicy food, and is diabetic. As further shown, server 150 may store menu information that indicates characteristics of menu items associated with a venue in which mobile device 110 is located (e.g., shown as Joe's Restaurant). For example, the menu information may indicate whether a menu item contains peanuts or another type of ingredient, whether a menu item is salty or has another characteristic, whether a menu item is spicy or has another taste characteristic, whether the menu item has previously caused a biological indicator to satisfy a threshold (e.g., an insulin spike, an increase in blood pressure, etc.), and/or the like.

As shown by reference number 740, server 150 may provide recommended health options to mobile device 110. As shown by reference number 750, mobile device 110 may output the recommended health options (e.g., via a user interface). For example, and as shown, the health options indicate that at Joe's Restaurant, the user should try the jerk chicken (e.g., because the jerk chicken is spicy, does not contain peanuts, is not salty, and will not cause an insulin spike). Further, the health options indicate that the user should avoid the peanut curry (e.g., because the peanut curry contains peanuts), should avoid the soup (e.g., because the soup is salty), and should avoid the blueberry muffin (e.g., because the blueberry muffin caused an insulin spike for one or more other users).

In some aspects, the health options may be ranked from most preferred to least preferred, or in some other manner. In some aspects, a health option may be displayed in association with a level of health risk associated with the health option (e.g., a menu item that may cause an allergic reaction may be associated with a high risk, whereas a menu item that is salty may be associated with a low risk). Additionally, or alternatively, health options (e.g., menu items) may be provided in association with a calorie count, a sugar content, a salt content, and/or the like.

In some aspects, display of the health options or another health alert by mobile device 110 may be triggered based on mobile device 110 being at a particular location, entering a particular venue, detecting performance of a particular activity, and/or the like. In some aspects, mobile device 110 may vibrate or otherwise provide an indication that the health alert has been received. In some aspects, the health alert may be provided based on a health application being installed on and/or executing on mobile device 110.

In this way, a user of mobile device 110 may be provided with predictive health alerts so that the user can make healthy decisions. For example, the user may avoid an unhealthy menu item or a menu item that will have a negative impact on the user's health (e.g., the salty soup or blueberry muffin that caused an insulin spike), may avoid a menu item to which the user is allergic (e.g., peanut curry), and may try a menu item that the user is likely to enjoy (e.g., the jerk chicken).

As indicated above, FIG. 7 is provided as an example. Other examples are possible and may differ from what was described in connection with FIG. 7.

FIG. 8 is a diagram illustrating an example process 800 for providing location-based health alerts, in accordance with various aspects of the present disclosure. In some implementations, one or more process blocks of FIG. 8 may be performed by mobile device 110. In some implementations, one or more process blocks of FIG. 8 may be performed by another device or a group of devices separate from or including mobile device 110, such as sensor device 130 and/or server 150.

As shown in FIG. 8, process 800 may include receiving sensor data (block 810). For example, mobile device 110 may receive sensor data. In some aspects, mobile device 110 may measure the sensor data using biometric sensor 235 of mobile device 110. Additionally, or alternatively, mobile device 110 may receive the sensor data from sensor device 130. As described elsewhere herein, the sensor data may include a measured biological indicator of a user of mobile device 110. In some aspects, the sensor data may include processed sensor data (e.g., raw sensor data that has been processed by sensor device 130 and/or mobile device 110).

In some aspects, server 150 may receive the sensor data. For example, server 150 may receive the sensor data from mobile device 110. Additionally, or alternatively, server 150 may receive the sensor data from sensor device 130 (e.g., a sensor device that communicates with base station 140). When server 150 receives the sensor data from sensor device 130, server 150 may determine a mobile device 110 associated with sensor device 130 (e.g., based on a mobile device identifier that identifies a mobile device 110 associated with sensor device 130). In some aspects, server 150 may provide the sensor data to mobile device 110.

As further shown in FIG. 8, process 800 may include determining, based on the sensor data, that a biological indicator satisfies a threshold (block 820). For example, mobile device 110 may determine that a biological indicator, represented by the sensor data, satisfies a threshold (e.g., an absolute threshold or a relative threshold). In some aspects, mobile device 110 may store one or more thresholds corresponding to one or more biological indicators. In some aspects, a threshold may be input by a user of mobile device 110. In some aspects, a threshold may be determined based on a default threshold. In some aspects, a biological indicator may be associated with more than one threshold (e.g., a low threshold, a high threshold, etc.). Mobile device 110 may compare a measured biological indicator to the threshold to determine whether the measured biological indicator satisfies the threshold (e.g., is greater than the threshold, is greater than or equal to the threshold, is equal to the threshold, is less than or equal to the threshold, is less than the threshold, etc.). In some aspects, mobile device 110 may determine whether the biological indicator satisfies the threshold for more than a particular amount of time, whether a particular quantity of successive biological indicators satisfies the threshold, and/or the like.

In some aspects, server 150 may determine that the biological indicator satisfies a threshold (e.g., in a similar manner as described above). For example, server 150 may receive sensor data from mobile device 110, and may determine that a biological indicator (e.g., included in the sensor data) satisfies a threshold. In some aspects, server 150 may provide information, indicating that the biological indicator satisfies the threshold, to mobile device 110.

As further shown in FIG. 8, process 800 may include requesting and receiving user input based on determining that the biological indicator satisfies the threshold (block 830). For example, mobile device 110 may request user input based on determining that the biological indicator satisfies the threshold. In some aspects, mobile device 110 may prompt a user for user input via a display and/or user interface of mobile device 110. For example, mobile device 110 may display a user interface and provide an input mechanism for a user to indicate an activity being performed by the user, a venue at which the user is located, and/or the like. In some aspects, mobile device 110 may provide an indication of the measured biological indicator for display. A user may interact with mobile device 110 to provide user input, and mobile device 110 may receive the user input based on the user interaction. Additionally, or alternatively, mobile device 110 may output a health alert to alert the user that the biological indicator satisfies the threshold, and may recommend that the user modify or stop an activity associated that caused the biological indicator to satisfy the threshold.

In some aspects, server 150 may request and receive user input based on determining that the biological indicator satisfies the threshold. For example, server 150 may determine that the biological indicator satisfies the threshold, and may provide a message to mobile device 110 requesting the user input. Mobile device 110 may obtain the user input (e.g., as described above), and may provide the user input to server 150. Additionally, or alternatively, mobile device 110 may output a health alert to alert the user that the biological indicator satisfies the threshold, as described above.

As an example, in the case of a blood pressure alert, how mobile device 110 may request and/or receive user input to determine if the cause of the blood pressure alert is related to an activity (e.g., a temporary spike due to exercise) or to a substance eaten. If the blood pressure alert was caused by an activity, mobile device 110 may provide output to advise the user to slow or stop the activity, and/or may flag the activity as being associated with a blood pressure alert. In some aspects, mobile device 110 may keep track of sensor data, such as PDR or other sensor measurements, and may use such sensor data to predict future events, such as predicted blood pressure alerts related to an activity, such as a use running past a certain speed, weightlifting, and/or the like. If the blood pressure alert was caused by a substance eaten, mobile device 110 may immediately provide a health alert to warn the user to stop eating whatever it is that is causing the health issue. Additionally, or alternatively, mobile device 110 may output a menu to permit the user to identify, on the menu, an item that is causing the problem.

In this way, when the user returns to a venue, mobile device 110 may present an option to pull up the menu associated with that menu (e.g., rather than a generic health warning) with flags associated with items that cause health issues. Additionally, or alternatively, information output by mobile device 110 may be contributed by multiple users. In this case, mobile device 110 may use statistics, such as number of reports for a particular condition for a particular item, a date of the reports, or an age of the reports, and/or the like. In this case, if a venue changes a menu item, such as by changing a recipe, old data that is no longer relevant will eventually age out and no longer be reported.

Additionally, or alternatively, mobile device 110 and/or server 150 may generate a message (e.g., an email message, an SMS message, etc.), and may provide the message to a venue (e.g., an owner, manager, etc. associated with the venue) to alert the venue that a specific menu item is causing problems. In some aspects, such a message may be provided periodically so that the venue can change a recipe. In some aspects, such a message may be provided immediately so that the venue can replace the dish with something less salty, spicy, etc. In some aspects, the venue may provide a message to server 150 to indicate that a recipe has been adjusted (e.g., to reduce salt, spiciness, MSG, etc.). In this way, older and less relevant message may be aged out and not reported. In some aspects, a venue may be permitted to provide input (e.g., to server 150) to provide menu information (e.g., information that identifies menu items, information that identifies food contents, such as an amount of salt, sugar and/or spice).

As further shown in FIG. 8, process 800 may include determining a location or a venue associated with a mobile device that received the sensor data (block 840). For example, mobile device 110 may determine a location of mobile device 110 (e.g., based on information received from GNSS satellites 120). Additionally, or alternatively, mobile device 110 may determine a venue associated with mobile device 110. For example, mobile device 110 may use a data structure, stored locally on mobile device 110 or remote from mobile device 110 (e.g., stored by server 150 or another device), to determine a venue based on a location.

In some aspects, mobile device 110 may identify a venue based on detecting an access point (e.g., a Wi-Fi access point) associated with the venue. For example, mobile device 110 may use a data structure, stored locally on mobile device 110 or remote from mobile device 110 (e.g., stored by server 150 or another device), to determine a venue based on an access point. For example, the data structure may store information that identifies associations between access points (e.g., using an access point identifier, such as an access point name, a network name, a service set identifier (SSID), and/or the like) and venues.

In some aspects, server 150 may determine a location and/or a venue associated with mobile device 110. For example, mobile device 110 may provide information that identifies the location to server 150. In some aspects, mobile device 110 may provide information that identifies a venue to server 150. Additionally, or alternatively, server 150 may use the location to identify a venue associated with the location (e.g., using a data structure that associates locations and venues and/or performing a search based on the location).

As further shown in FIG. 8, process 800 may include storing or providing health information in association with the location or the venue (block 850). For example, mobile device 110 may store health information in association with the location and/or the venue. The health information may be identified based on the sensor data and/or the user input. In some aspects, the health information may include the sensor data, a portion of the sensor data, the user input, a portion of the user input, and/or the like. In some aspects, mobile device 110 may provide the health information. For example, mobile device 110 may provide the health information to server 150 (e.g., for storage).

In some aspects, server 150 may store the health information. For example, server 150 may receive, from mobile device 110, the sensor data and/or the user input. Server 150 may identify the health information based on the sensor data and/or the user input, and may store the health information. Server 150 may store the health information is association with the location and/or the venue.

In this way, mobile device 110 and/or server 150 may populate a data structure that stores health information associated with a location and/or a venue. The data structure may be populated with health information, which may be used to provide health alerts to one or more mobile devices 110 when those mobile device(s) 110 are located at the location and/or the venue. In this way, a user of mobile device 110 can receive predictive health alerts associated with locations or venues, so that the user can make intelligent health-related decisions at those locations or venues.

Although FIG. 8 shows example blocks of process 800, in some implementations, process 800 may include additional blocks, fewer blocks, different blocks, or differently arranged blocks than those depicted in FIG. 8. Additionally, or alternatively, two or more of the blocks of process 800 may be performed in parallel.

FIG. 9 is a diagram illustrating another example process 900 for providing location-based health alerts, in accordance with various aspects of the present disclosure. In some implementations, one or more process blocks of FIG. 9 may be performed by server 150. In some implementations, one or more process blocks of FIG. 9 may be performed by another device or a group of devices separate from or including server 150, such as mobile device 110.

As shown in FIG. 9, process 900 may include receiving information that identifies a location associated with a mobile device (block 910). For example, server 150 may receive, from mobile device 110, information that identifies a location associated with mobile device 110. For example, mobile device 110 may determine a location of mobile device 110 (e.g., based on information received from GNSS satellites 120, and may provide information that identifies the location to server 150. The information that identifies the location may include, for example, GPS data (e.g., a latitude, longitude, and/or altitude), a street address, a name of a location and/or venue, and/or the like.

In some implementations, the location may be associated with a list that identifies one or more venues (e.g., restaurants) within a threshold geographic proximity of the location. In this case, server 150 may store and/or receive the list of venues based on the information that identifies the location. In some implementations, server 150 may request the list of venues from another device. Server 150 may identify health information and/or a health alert based on the list of venues, as described in more detail below. Server 150 may provide the health information and/or the health alert to mobile device 110 so that a user can use the health information and/or the health alert to decide on a venue.

As further shown in FIG. 9, process 900 may include determining a venue associated with the location (block 920). For example, server 150 may use a location, associated with mobile device 110, to identify a venue associated with the location (e.g., using a data structure that associates locations and venues and/or performing a search based on the location). Additionally, or alternatively, mobile device 110 may determine the venue, and may provide information that identifies the venue to server 150. In some cases, a venue may be determined as described above in block 910 (e.g., based on a street address, based on a name of the venue, based on an Internet search of a location, and/or the like). In some aspects, when a venue is determined based on a location, server 150 may determine whether the location is within a threshold distance of a particular location, may determine the location with a threshold level of confidence, or the like.

As further shown in FIG. 9, process 900 may include identifying health information, associated with the venue, based on data previously received in association with the venue (block 930). For example, server 150 may identify health information associated with the venue. The health information may be identified based on data previously received in association with the venue (e.g., previously received from mobile device 110). For example, server 150 may receive sensor data and/or user input from mobile device 110, and may store health information, based on the sensor data and/or user input, in association with a venue where mobile device 110 is located. At a later time, server 150 may receive information that identifies a location and/or a venue associated with that mobile device 110 and/or a different mobile device 110, and may identify the health information that was previously stored in association with the venue.

In some aspects, the health information could be provided and/or sorted specifically for a user, such as based on that user's particular past results, and/or based on group data combining all users' historical data. User-specific data may be especially helpful for exercise information, which may be user-specific. In some aspects, user-specific data may be stored locally by mobile device 110. In some aspects, group data that combines input from other people can also be made available. Group data may be especially helpful for menu-related data where input from multiple people on various menu items is important so that a particular user don't have to actually eat the menu item to know whether the menu item will cause trouble. Group data may be useful for activities intended to evoke a physiological response, such as carnival rides. In some aspects, the user may be given a choice to receive user-specific data, group data, or both sets of data.

In some aspects, to prevent malicious attacks on a venue, data for a particular user may be analyzed for consistency with a particular condition or consistency with other people's reports, particularly when being used for group data. So, if a user only reports salty items at one venue but does not report salty items at other venues that serve known salty items or if a user provides a bunch of bad reports at a single venue without similar reports at other venues, that data might be treated as lower in confidence or perhaps even not combined into the group data. In this case, such data may still be used for user specific-data.

As further shown in FIG. 9, process 900 may include providing a health alert based on the health information (block 940). For example, server 150 may generate and/or provide a health alert based on the health information. In some aspects, server 150 may provide the health alert to a mobile device 110 from which the data was previously received. In some aspects, server 150 may provide the health alert to a different mobile device 110 (e.g., based on the different mobile device 110 being located at a venue associated with the health information). In some aspects, the health alert may include the health information. For example, server 150 may provide the health information to mobile device 110, and mobile device 110 may output a health alert based on the health information. As another example, the health alert may include a measured biological indicator and/or user input previously received in association with a venue. In some aspects, the health alert may include a recommended health option, such as a recommendation regarding food, a recommendation regarding a drink, a recommendation regarding an exercise, a recommendation regarding an activity, and/or the like. In some aspects, server 150 and/or mobile device 110 may selectively provide the health alert based on user profile information. For example, if a user is not diabetic, then server 150 and/or mobile device 110 may prevent health alerts associated with diabetes from being provided, thereby conserving computing resources and/or network resources.

In this way, a user of mobile device 110 may be provided with predictive health alerts so that the user can make healthy decisions. For example, the user may avoid eating an unhealthy food, may avoid a particular venue for health reasons, may take medication prior to visiting a venue or participating in an activity at the venue, and/or the like.

Although FIG. 9 shows example blocks of process 900, in some implementations, process 900 may include additional blocks, fewer blocks, different blocks, or differently arranged blocks than those depicted in FIG. 9. Additionally, or alternatively, two or more of the blocks of process 900 may be performed in parallel.

FIG. 10 is a diagram illustrating another example process 1000 for providing location-based health alerts, in accordance with various aspects of the present disclosure. In some implementations, one or more process blocks of FIG. 10 may be performed by server 150. In some implementations, one or more process blocks of FIG. 10 may be performed by another device or a group of devices separate from or including server 150, such as mobile device 110.

As shown in FIG. 10, process 1000 may include receiving multiple biological indicators, associated with multiple users, measured in association with a location or a venue (block 1010). For example, server 150 may receive, from multiple mobile devices 110, measured biological indicators and/or sensor data that includes the multiple biological indicators. For example, biological indicators of multiple users may be measured (e.g., at different times) by different sensor devices 130 and provided to server 150 by multiple mobile devices 110. The multiple mobile devices 110 may be located in a particular venue or location when the biological indicators are measured.

In some implementations, server 150 may receive health reports from multiple mobile devices 110. In some implementations, a health report may include a biological indicator, measured in association with a user of mobile device 110, and information that identifies a location associated with mobile device 110. In this case, server 150 may determine a venue associated with the location, as described elsewhere herein. Additionally, or alternatively, a health report may include the biological indicator and information that identifies the venue. Additionally, or alternatively, a health report may include the biological indicator, information that identifies the location, and information that identifies the venue. Additionally, or alternatively, a health report may include information that identifies an activity performed by the user. Additionally, or alternatively, a health report may include user input provided by a user of mobile device 110. As described in more detail below, server device 150 may store received health reports. When aggregated, such health reports may cover multiple types of biological indicators, multiple locations, multiple venues, and/or multiple activities.

In some implementations, a health report may be anonymized and/or encrypted (e.g., by mobile device 110 and/or server 150) to protect user privacy. In some implementations, a user may provide input (e.g., to mobile device 110 or another device) indicating whether user data, such as the health report, is to be anonymized and/or encrypted. In some cases, the user may decide not to anonymize health reports associated with the user so that the user can be provided with personalized health alerts.

As further shown in FIG. 10, process 1000 may include storing health information, in association with the location or the venue, based on the multiple biological indicators (block 1020). For example, server 150 may store health information in association with the location and/or the venue. The health information may be identified based on the sensor data, user input, and/or the multiple biological indicators, as described elsewhere herein. For example, the health information may include a measured biological indicator (e.g., a measured blood pressure or other biological indicators described herein), user input (e.g., "The soup is salty"), or other health information described herein. In some aspects, the health information may include the sensor data, a portion of the sensor data, the user input, a portion of the user input, one or more measured biological indicators, and/or the like. Server 150 may store the health information in association with the location and/or the venue.

As an example, health information may include food information associated with a location, venue, and/or menu item. Additionally, or alternatively, health information may include notes provided by users about which item on a dish is causing a problem, as a given order may contain more than one item (e.g., a note to avoid the sauce, the side dish, etc.). In some aspects, the health information may indicate a measure or degree of the biological reaction of one or more users (e.g., to rate items as causing extreme responses versus moderate responses). In some aspects, the health information may include a user identifier to associate a user with that users' own records that the user-specific information can be identified. In some aspects, the health information may be encrypted or otherwise protected.

In some aspects, the health information may include an activity indicator associated with a venue and/or location, such as a particular gym or hiking trail. In some aspects, the activity indicator may be independent of location and/or venue. For example, if a user is running, mobile device 110 may use one or more sensors, such as motion/location sensor 230, to detect and/or record the activity. If mobile device 110 outputs a health alert for the activity, a sensor reading may be recorded for future detection of the same or similar activities. Additionally, or alternatively, the user may be queried as to the activity being performed. Additionally, or alternatively, the user may be alerted as to the condition that is causing the health alert, such as a blood pressure or a pulse over a particular threshold. Thus, an activity indicator may be linked to an activity itself and sensed via one or more sensors no matter where the activity occurs, may be linked to a location or venue (e.g., a gym, a set of stairs, a hiking trail, etc.), or may be linked to both. In some aspects, the one or more sensors may be pre-programmed to detect certain common activities, such as running, swimming, hiking up a grade (using a PDR and altimeter), and/or the like. In this case, the user may not need to be queried about what activity is being performed. Further, certain health alerts can be predicted, such as by the presence of a steep grade at a particular location, even if no prior data has been received in association with that that location.

In some implementations, server 150 may store the health reports, received in association with a location and/or a venue, as the health information. In this way, server 150 can provide (e.g., to mobile device 110) a list of biological indicators and/or user input associated with the location, venue, and/or activity. In some implementations, server 150 may apply one or more rules to determine severity levels associated with different biological indicators, such that server 150 can provide the list of biological indicators in an order based on the severity levels. Additionally, or alternatively, server 150 may determine an order for the list of biological indicators and/or user input based on user feedback (e.g., user likes or dislikes), based on a date and/or time at which a health report was received (e.g., to prioritize information received in more recent health reports), and/or the like.

In some implementations, server 150 may remove, from the list, information received in health reports that are older than a particular time (e.g., information included in health reports received over a year in the past). Additionally, or alternatively, server 150 may store a particular quantity of health reports, and may remove an oldest health report when a new health report is received. Additionally, or alternatively, server 150 may remove health reports after a threshold quantity of health reports are received that indicate that older health reports are no longer relevant. For example, old health reports may indicate that a particular menu item cause a spike in blood pressure, while new health reports may not indicate such spike in blood pressure (e.g., because a recipe of the menu item has changed). After receiving a threshold quantity of such reports that indicate no spike in blood pressure, server 150 may remove the old reports that indicate the spike in blood pressure. In this way, the health information may be kept up-to-date.

In some implementations, server 150 may analyze and/or organize the health reports to store the health information. For example, server 150 may store health information the identifies a list of biological indicators affected by a location, venue, or activity, may store health information that identifies a list of locations that impact a particular biological indicator, may store health information that identifies a list of venues that impact a particular biological indicator, may store health information that identifies a list of activities that impact a particular biological indicator, may store health information that identifies a list of locations, venues, or activities that impact a particular biological indicator by a threshold amount, may store health information that identifies a list of locations, venues, or activities that impact multiple biological indicators, and/or the like. As an example, server 150 may aggregate health information from health reports associated with a particular activity at a particular venue, such as eating a particular menu item at a particular restaurant.

In some implementations, server 150 may aggregate values of biological indicators to store various statistics related to the biological indicators as the health information, such as mean, median, standard deviation, etc. For example, server 150 may determine an average value (e.g., a mean or median value) of a biological indicator (e.g., average blood pressure, average change in blood pressure, average glucose level, average change in glucose level, etc.), a maximum value of a biological indicator, a minimum value of a biological indicator, and/or the like. Server 150 may store such various statistics, as the health information, in association with a location, venue, or activity. For example, server 150 may receive information that identifies heart rates at various locations along a hiking trail from a plurality of mobile devices, and server 150 may use this information to determine an average heart rate at one or more of those locations.

Additionally, or alternatively, server 150 may group health information based on user characteristics, and may determine various statistics for a particular characteristic group. For example, server 150 may receive data from users with a wide range of ages, such as five to seventy five years old, so rather than determine an average heart rate at a particular location for all users of all ages, server 150 may group data for users between, for example, ages twenty to twenty-five, ages twenty-five to thirty, etc. and then determine the average heart rate for that group at that particular location.

Additionally, or alternatively, server 150 may store information that identifies a quantity of health incidents associated with a location, venue, or activity (e.g., a quantity of health reports received that satisfy a condition, such as a biological indicator satisfying a threshold). For example, server 150 may store information that identifies a quantity of health incidents over a time period (e.g., 1 month, 6 months, 1 year, all time, etc.), a rate of health incidents (e.g., a quantity of health incidents reported per month, year, etc.), and/or the like.

In this way, server 150 may populate a database that stores health information associated with a location and/or a venue. Server 150 may populate the database with health information received from multiple mobile devices 110 associated with multiple users. This health information be used to provide health alerts to mobile devices 110 when those mobile devices 110 are located at the location and/or the venue. In this way, a user of mobile device 110 can receive predictive health alerts associated with locations or venues even if the user has not previously visited the location or venue (e.g., based on health information associated with other users, such as other users who have user profile information in common with the user).

Although FIG. 10 shows example blocks of process 1000, in some implementations, process 1000 may include additional blocks, fewer blocks, different blocks, or differently arranged blocks than those depicted in FIG. 10. Additionally, or alternatively, two or more of the blocks of process 1000 may be performed in parallel.

FIG. 11 is a diagram illustrating another example process 1100 for providing location-based health alerts, in accordance with various aspects of the present disclosure. In some implementations, one or more process blocks of FIG. 11 may be performed by server 150. In some implementations, one or more process blocks of FIG. 11 may be performed by another device or a group of devices separate from or including server 150, such as mobile device 110.

As shown in FIG. 11, process 1100 may include receiving, from a mobile device, information that identifies a location (block 1110). For example, server 150 may receive, from mobile device 110, information that identifies a location associated with mobile device 110. For example, mobile device 110 may determine a location of mobile device 110

(e.g., based on information received from GNSS satellites 120), and may provide information that identifies the location to server 150.

As further shown in FIG. 11, process 1100 may include determining a venue based on the location (block 1120). For example, server 150 may use the location, associated with mobile device 110, to identify a venue associated with the location (e.g., using a data structure that associates locations and venues). Additionally, or alternatively, mobile device 110 may determine the venue, and may provide information that identifies the venue to server 150. The venue may be the same as a venue associated with mobile devices 110 that provided biological indicators to server 150 (e.g., as described in connection with FIG. 10), and server 150 may use the biological indicators to generate a health alert to be provided to mobile device 110, as described below.

As further shown in FIG. 11, process 1100 may include identifying health information, associated with the venue, based on multiple biological indicators, associated with multiple users, measured in association with the location or the venue (block 1130). For example, server 150 may identify health information associated with the venue. The health information may be previously stored by server 150 based on the multiple biological indicators measured in association with the venue, as described above. In some aspects, server 150 may obtain the health information based on storing the health information in association with the venue. In some aspects, server 150 may retrieve the health information (e.g., a from a data structure).

As further shown in FIG. 11, process 1100 may include providing a health alert based on the health information (block 1140). For example, server 150 may generate and/or provide a health alert based on the health information. In some aspects, server 150 may provide the health alert to a mobile device 110, and mobile device 110 may output the health alert, despite not having previously received data from mobile device 110 (e.g., based on data, such as biological indicators, received from other mobile devices 110).

Additionally, or alternatively, server 150 may receive, from mobile device 110, a query associated with the health information, and may provide the health alert based on the query. For example, a user may interact with mobile device 110 to request locations, venues, or activities (e.g., menu items) that do not have a negative impact on a particular biological indicator, that do not have a negative impact on any biological indicators, and/or the like. As another example, the user may interact with mobile device 110 to identify a location, venue, or activity, and server 150 may return health information associated with the identified location, venue, or activity. In some implementations, server 150 may provide, as the health alert, information that identifies a quantity of health incidents associated with a location, venue, or activity.

In this way, server 150 may populate a database that stores health information associated with a location and/or a venue. Server 150 may populate the database with health information received from multiple mobile devices 110 associated with multiple users. This health information be used to provide health alerts to mobile devices 110 when those mobile devices 110 are located at the location and/or the venue. In this way, a user of mobile device 110 can receive predictive health alerts associated with locations or venues even if the user has not previously visited the location or venue (e.g., based on health information associated with other users, such as other users who have user profile information in common with the user).

Although FIG. 11 shows example blocks of process 1100, in some implementations, process 1100 may include additional blocks, fewer blocks, different blocks, or differently arranged blocks than those depicted in FIG. 11. Additionally, or alternatively, two or more of the blocks of process 1100 may be performed in parallel.

FIG. 12 is a diagram illustrating another example process 1200 for providing location-based health alerts, in accordance with various aspects of the present disclosure. In some implementations, one or more process blocks of FIG. 12 may be performed by mobile device 110. In some implementations, one or more process blocks of FIG. 12 may be performed by another device or a group of devices separate from or including mobile device 110, such as server 150.

As shown in FIG. 12, process 1200 may include determining, based on sensor data, an activity associated with a user of a mobile device (block 1210). For example, mobile device 110 may use sensor data to determine an activity being performed by a user of mobile device 110. As an example, mobile device 110 may use sensor data to determine that a user is sitting down (e.g., at a restaurant, based on location information and/or a lack of movement of mobile device 110), that a user is eating (e.g., based on detecting a repetitive hand movement), that a user is exercising (e.g., based on a movement of mobile device 110), and/or the like.

In some aspects, mobile device 110 may identify the activity, and may provide information identifying the activity to server 150. Additionally, or alternatively, server 150 may determine the activity based on sensor data received from mobile device 110. In some aspects, server 150 may receive data from mobile device 110, such as sensor data, processed sensor data, user input, data received in association with a venue, and/or the like, and may determine the activity based on the data. The activity may include, for example, eating, drinking, exercising, and/or the like.

In some aspects, the activity may be identified based on sensor data from mobile device 110, and information identifying the activity and/or activity parameters may be provided to server 150. In some aspects, server 150 may send a periodically refreshed cache of health alert parameters to mobile device 110, and mobile device 110 may use these health alert parameters to determine locally when a health alert is warranted. For example, mobile device 110 may determine that running faster than a particular speed or running up a particular grade will cause a user's blood pressure to exceed a threshold. Such information may be stored by mobile device 110, by server 150, or by both. Thus may result in a set of rules (e.g., stored locally on mobile device 110) that indicate when to trigger a health alert. In some aspects, mobile device 110 may not send all the sensor data to server 150, and may detect the activity locally on mobile device 110, thereby conserving network resources.

As further shown in FIG. 12, process 1200 may include identifying health information based on the activity and data previously received in association with the activity (block 1220). For example, mobile device 110 and/or server device 150 may identify health information based on the activity. The health information may be identified based on data previously received in association with the activity (e.g., previously received by or from mobile device 110). Additionally, or alternatively, the health information may be identified based on a current biological indicator (e.g., blood pressure) measured by one or more sensors associated with mobile device 110. For example, mobile device 110 may determine a biological indicator, may provide the biological indicator to server 150. Server 150 may identify health information based on the biological indicator (e.g., by filtering a collection of health information using the biological indicator), and may provide the health information to mobile device 110. In some aspects, mobile device 110 may receive health information from server 150 and may filter the health information, based on a measured biological indicator, to generate a health alert.

For example, mobile device 110 and/or server 150 may receive sensor data and/or user input, and may store health information, based on the sensor data and/or user input, in association with an activity being performed by a user of mobile device 110. In some aspects, the activity may be determined based on sensor data. Additionally, or alternatively, the activity may be determined based on user input that identifies the activity. At a later time, server 150 may receive information that identifies an activity being performed by a user of mobile device 110 and/or a different mobile device 110, and may identify the health information that was previously stored in association with the activity. In some aspects, the health information, stored in association with the activity, may also be stored in association with a location and/or a venue where mobile device 110 is located.

In some implementations, mobile device 110 and/or server 150 may store the health information in association with the activity as well as a location and/or a venue associated with the biological indicator. Additionally, or alternatively, mobile device 110 and/or server 150 may analyze health reports to determine whether a particular biological indicator is impacted by an activity or by a location or venue, and may output such information. In this way, a user may determine whether a change in a biological indicator is triggered by a particular activity, a particular location, or a particular venue.

As further shown in FIG. 12, process 1200 may include providing a health alert based on the health information (block 1230). For example, mobile device 110 and/or server 150 may generate and/or provide a health alert based on the health information. In some aspects, server 150 may provide the health alert to a mobile device 110 from which the data was previously received. In some aspects, server 150 may provide the health alert to a different mobile device 110 (e.g., based on the different mobile device 110 indicating that a user is performing the activity associated with the health information). In some aspects, the health alert may include the health information. For example, the health alert may include a measured biological indicator and/or user input previously received in association with an activity.

In this way, a user of mobile device 110 may be provided with predictive health alerts so that the user can make healthy decisions regarding an activity. For example, the user may avoid participating in an activity that has a negative impact on the user's health, may be encouraged to participate in an activity that has a positive impact on the user's health, and/or the like.

Although FIG. 12 shows example blocks of process 1200, in some implementations, process 1200 may include additional blocks, fewer blocks, different blocks, or differently arranged blocks than those depicted in FIG. 12. Additionally, or alternatively, two or more of the blocks of process 1200 may be performed in parallel.

FIG. 13 is a diagram illustrating another example process 1300 for providing location-based health alerts, in accordance with various aspects of the present disclosure. In some implementations, one or more process blocks of FIG. 13 may be performed by server 150. In some implementations, one or more process blocks of FIG. 13 may be performed by another device or a group of devices separate from or including server 150, such as mobile device 110.

As shown in FIG. 13, process 1300 may include receiving information that identifies a location or a venue associated with a mobile device (block 1310). For example, server 150 may receive, from mobile device 110, information that identifies a location associated with mobile device 110. For example, mobile device 110 may determine a location of mobile device 110 (e.g., based on information received from GNSS satellites 120), and may provide information that identifies the location to server 150. In some aspects, server 150 may use the location to identify a venue associated with the location (e.g., using a data structure that associates locations and venues). Additionally, or alternatively, mobile device 110 may determine the venue, and may provide information that identifies the venue to server 150.

As further shown in FIG. 13, process 1300 may include identifying user profile information associated with a user of the mobile device (block 1320). For example, server 150 may use a data structure (e.g., stored by server 150 or another device) to identify user profile information associated with a user of mobile device 110. In some aspects, the data structure may associate a mobile device identifier, of mobile device 110, with the user profile information. Additionally, or alternatively, server 150 may receive the user profile information from mobile device 110.

The user profile information may indicate a health condition of a user of mobile device 110 (e.g., diabetic, allergies, high blood pressure, one or more medications being taken by the user, etc.), health preferences and/or activity preferences associated with the user (e.g., a type of food or drinks that the user enjoys, a manner in which the user likes his or her meals prepared, a type of exercise that the user enjoys, etc.), and/or the like. Additionally, or alternatively, the user profile information may include information from one or more health reports received in association with a user. Additionally, or alternatively, the user profile information may include information from one or more health alerts provided to mobile device 110 associated with a user.

In some aspects, the user profile information may include information that indicates whether a user flagged a particular menu item as causing a problem.

Additionally, or alternatively, the user profile information may include information that indicates whether a user flagged a particular menu item as safe. For example, the user may send a report (e.g., a report initiated by the user) indicating that one or more menu items did not cause an adverse reaction (e.g., no sugar crash, no blood pressure issues, no allergic reaction for a particular allergy, etc.). In this way, server 150 may be able to determine which items are safe to east for people with particular sensitivities and/or allergies. For example, people that are allergic to shrimp might worry that a sauce or other menu item includes a particular ingredient (e.g., shrimp, pork, peanuts, etc.). By marking items as safe, these users may be able to easily determine whether the menu items contain these ingredients.

As further shown in FIG. 13, process 1300 may include identifying health information, associated with the location or the venue, based on the user profile information and data previously received in association with the location or the venue (block 1330). For example, server 150 may identify health information associated with the location and/or the venue. The health information may be identified based on data previously received in association with the location and/or the venue (e.g., previously received from mobile device 110).

Additionally, or alternatively, server 150 may identify the health information based on user profile information. For example, when server 150 stores health information, the health information may be associated with user profile information. When identifying the health information, server 150 may identify the health information based on a characteristic of user profile information associated with a user of mobile device 110 matching a characteristic of stored user profile information associated with the health information (e.g., that the user is diabetic, has a particular allergy, etc.).

As further shown in FIG. 13, process 1300 may include providing a health alert based on the health information (block 1340). For example, server 150 may generate and/or provide a health alert based on the health information. In some aspects, server 150 may provide the health alert to a mobile device 110 from which the data was previously received. In some aspects, server 150 may provide the health alert to a different mobile device 110 (e.g., based on the different mobile device 110 being associated with a user that has user profile information that matches user profile information of a user of mobile device 110).

In this way, a user of mobile device 110 may be provided with predictive health alerts so that the user can make healthy decisions. The predictive health alerts can be generated based on user profile information to provide more accurate and relevant health alerts.

Although FIG. 13 shows example blocks of process 1300, in some implementations, process 1300 may include additional blocks, fewer blocks, different blocks, or differently arranged blocks than those depicted in FIG. 13. Additionally, or alternatively, two or more of the blocks of process 1300 may be performed in parallel.

Aspects described herein use a geographic location associated with a user's mobile device to provide the user with predictive health alerts associated with the geographic location or a venue at the geographic location. Such health alerts may be determined based on data previously received in association with the geographic location or venue, such as input provided by the user (e.g., via the mobile device), input provided by other users, measured biological indicators of the user or other users, and/or the like. In this way, a user may be alerted of activities that would have a negative impact on the user's health, and may avoid such activities.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," and/or the like are intended to be open-ended terms. Further, the phrase "based on" is intended to mean "based, at least in part, on" unless explicitly stated otherwise.

What is claimed is:

1. A mobile device, comprising:
a memory; and
one or more processors coupled to the memory, wherein the one or more processors are configured to:
  determine that a biological indicator satisfies a threshold at a first time;
  provide a request for user input based on determining that the biological indicator satisfies the threshold;
  receive the user input;
  provide data, including the biological indicator and the user input, for storage in association with information identifying a venue;
  determine a location associated with the mobile device at a second time after the first time;
  access health information associated with the venue based on determining the location,
    wherein the health information is based on the data previously provided in association with the venue,
    wherein the venue is associated with the location, and
    wherein the data comprises the biological indicator previously measured in association with the venue at the first time; and
  provide, based on the health information, a health alert that includes the user input.

2. The mobile device of claim 1, wherein the one or more processors are configured to:

determine an activity being performed by a user of the mobile device; and
access the health information based on the activity.

3. The mobile device of claim 2, wherein the one or more processors are configured to:
receive sensor data from a sensor associated with the mobile device; and
determine the activity based on the sensor data.

4. The mobile device of claim 1, wherein the biological indicator is measured by a sensor associated with the mobile device.

5. The mobile device of claim 1, wherein the health information is identified based on the biological indicator measured by one or more sensors associated with the mobile device.

6. The mobile device of claim 1, wherein the one or more processors are configured to:
identify user profile information associated with a user of the mobile device; and
access the health information based on the user profile information.

7. The mobile device of claim 1, wherein the one or more processors are configured to:
determine a plurality of health options associated with the venue;
determine, based on the health information, one or more recommended health options of the plurality of health options; and
wherein the health alert includes information that identifies the one or more recommended health options.

8. The mobile device of claim 7, wherein the one or more recommended health options indicate at least one of:
a recommendation regarding food,
a recommendation regarding a drink,
a recommendation regarding exercise, or
any combination thereof.

9. A method, comprising:
determining, by a mobile device, that a biological indicator satisfies a threshold at a first time;
providing, by the mobile device, a request for user input based on determining that the biological indicator satisfies the threshold;
receiving, by the mobile device, the user input;
providing, by the mobile device, data, including the biological indicator and the user input, for storage in association with information identifying a venue;
determining, by the mobile device, a location associated with the mobile device at a second time after the first time;
accessing, by the mobile device, health information associated with the venue based on determining the location,
wherein the health information is based on the data previously provided in association with the venue,
wherein the venue is associated with the location, and
wherein the data comprises the biological indicator previously measured in association with the venue at the first time; and
providing, by the mobile device and based on the health information, a health alert that includes the user input.

10. The method of claim 9, wherein the biological indicator is measured by a sensor associated with the mobile device.

11. The method of claim 9, further comprising:
identifying user profile information associated with a user of the mobile device; and
accessing the health information based on the user profile information.

12. The method of claim 9, further comprising:
determining an activity being performed by a user of the mobile device; and
accessing the health information based on the activity.

13. The method of claim 12, further comprising:
receiving sensor data from a sensor associated with the mobile device; and
determining the activity based on the sensor data.

14. The method of claim 9, further comprising:
determining a plurality of health options associated with the venue;
determining, based on the health information, one or more recommended health options of the plurality of health options; and
wherein the health alert includes information that identifies the one or more recommended health options.

15. The method of claim 14, wherein the one or more recommended health options indicate at least one of:
a recommendation regarding food,
a recommendation regarding a drink,
a recommendation regarding exercise, or
any combination thereof.

16. An apparatus, comprising:
means for determining that a biological indicator satisfies a threshold at a first time;
means for providing a request for user input based on determining that the biological indicator satisfies the threshold;
means for receiving the user input;
means for providing data, including the biological indicator and the user input, for storage in association with information identifying a venue;
means for determining a location associated with the apparatus at a second time after the first time;
means for accessing health information associated with the venue based on determining the location,
wherein the health information is based on the data previously provided in association with the venue,
wherein the venue is associated with the location, and
wherein the data comprises the biological indicator previously measured in association with the venue at the first time; and
means for providing, and based on the health information, a health alert that includes the user input.

17. The apparatus of claim 16, wherein the biological indicator is measured by a sensor associated with the apparatus.

18. The apparatus of claim 16, further comprising:
means for identifying user profile information associated with a user of the apparatus; and
means for accessing the health information based on the user profile information.

19. The apparatus of claim 16, further comprising:
means for determining an activity being performed by a user of the apparatus; and
means for accessing the health information based on the activity.

20. The apparatus of claim 19, further comprising:
means for receiving sensor data from a sensor associated with the apparatus; and
means for determining the activity based on the sensor data.

21. The apparatus of claim 16, further comprising:
means for determining a plurality of health options associated with the venue;
means for determining, based on the health information, one or more recommended health options of the plurality of health options; and
wherein the health alert includes information that identifies the one or more recommended health options.

22. The apparatus of claim 21, wherein the one or more recommended health options indicate at least one of:
a recommendation regarding food,
a recommendation regarding a drink,
a recommendation regarding exercise, or
any combination thereof.

23. A non-transitory computer-readable medium storing instructions, the instructions comprising:
one or more instructions that, when executed by one or more processors of a mobile device, cause the one or more processors to:
determine that a biological indicator satisfies a threshold at a first time;
provide a request for user input based on determining that the biological indicator satisfies the threshold;
receive the user input;
provide data, including the biological indicator and the user input, for storage in association with information identifying a venue;
determine a location associated with the mobile device at a second time after the first time;
access health information associated with the venue based on determining the location,
wherein the health information is based on the data previously provided in association with the venue, wherein the venue is associated with the location, and
wherein the data comprises the biological indicator previously measured in association with the venue at the first time; and
provide, based on the health information, a health alert that includes the user input.

24. The non-transitory computer-readable medium of claim 23, wherein the one or more instructions, when executed by the one or more processors, cause the one or more processors to:
determine an activity being performed by a user of the mobile device; and
access the health information based on the activity.

25. The non-transitory computer-readable medium of claim 24, wherein the one or more instructions, when executed by the one or more processors, cause the one or more processors to:
receive sensor data from a sensor associated with the mobile device; and
determine the activity based on the sensor data.

26. The non-transitory computer-readable medium of claim 23, wherein the biological indicator is measured by a sensor associated with the mobile device.

27. The non-transitory computer-readable medium of claim 23, wherein the health information is identified based on the biological indicator measured by one or more sensors associated with the mobile device.

28. The non-transitory computer-readable medium of claim 23, wherein the one or more instructions, when executed by the one or more processors, cause the one or more processors to:
identify user profile information associated with a user of the mobile device; and
access the health information based on the user profile information.

29. The non-transitory computer-readable medium of claim 23, wherein the one or more instructions, when executed by the one or more processors, cause the one or more processors to:
determine a plurality of health options associated with the venue;
determine, based on the health information, one or more recommended health options of the plurality of health options; and
wherein the health alert includes information that identifies the one or more recommended health options.

30. The non-transitory computer-readable medium of claim 29, wherein the one or more recommended health options indicate at least one of:
a recommendation regarding food,
a recommendation regarding a drink,
a recommendation regarding exercise, or
any combination thereof.

31. The non-transitory computer-readable medium of claim 23, wherein the health alert includes the biological indicator.

* * * * *